(12) United States Patent
Bradley et al.

(10) Patent No.: US 8,716,457 B2
(45) Date of Patent: May 6, 2014

(54) NUCLEOBASE CHARACTERISATION

(75) Inventors: Mark Bradley, Edinburgh (GB); Juan J. Diaz-Mochon, Edinburgh (GB)

(73) Assignee: The University Court of the University of Edinburgh (GB)

( * ) Notice: Subject to any disclaimer, the term of this patent is extended or adjusted under 35 U.S.C. 154(b) by 588 days.

(21) Appl. No.: 12/679,221

(22) PCT Filed: Sep. 19, 2008

(86) PCT No.: PCT/GB2008/003185
§ 371 (c)(1),
(2), (4) Date: Oct. 25, 2010

(87) PCT Pub. No.: WO2009/037473
PCT Pub. Date: Mar. 26, 2009

(65) Prior Publication Data
US 2011/0028337 A1 Feb. 3, 2011

(30) Foreign Application Priority Data
Sep. 19, 2007 (GB) .................................. 0718255.3

(51) Int. Cl.
*C12Q 1/68* (2006.01)
*C07G 3/00* (2006.01)
*C07H 21/00* (2006.01)

(52) U.S. Cl.
USPC ......... 536/4.1; 536/23.1; 536/24.3; 536/26.6; 435/6.1

(58) Field of Classification Search
USPC .................. 435/6.1; 536/4.1, 23.1, 24.3, 26.6
See application file for complete search history.

(56) References Cited

PUBLICATIONS

A. P. Martinez, et al.: "DL-Willardiine mustard" Journal of Medicinal Chemistry, vol. 11, No. 1, 1968, pp. 60-62.*
Ausin, et al.: "Synthesis of Amino- and Guanidino-G-clamp PNA Monomers" Organic Letters, vol. 4, No. 3, 2002, pp. 407.3-4075.*

* cited by examiner

*Primary Examiner* — Jezia Riley
(74) *Attorney, Agent, or Firm* — Schwegman Lundberg & Woessner, P.A.

(57) ABSTRACT

The present invention provides modified nucleobase compounds, modified nucleic acid mimetic compounds and various uses thereof. In addition, the invention provides methods for nucleobase characterisation, SNP characterisation and nucleic acid sequencing.

12 Claims, 19 Drawing Sheets

4 DNA Strands

PNA Strand Added

Add PNA-Aldehydes

Figure 1:
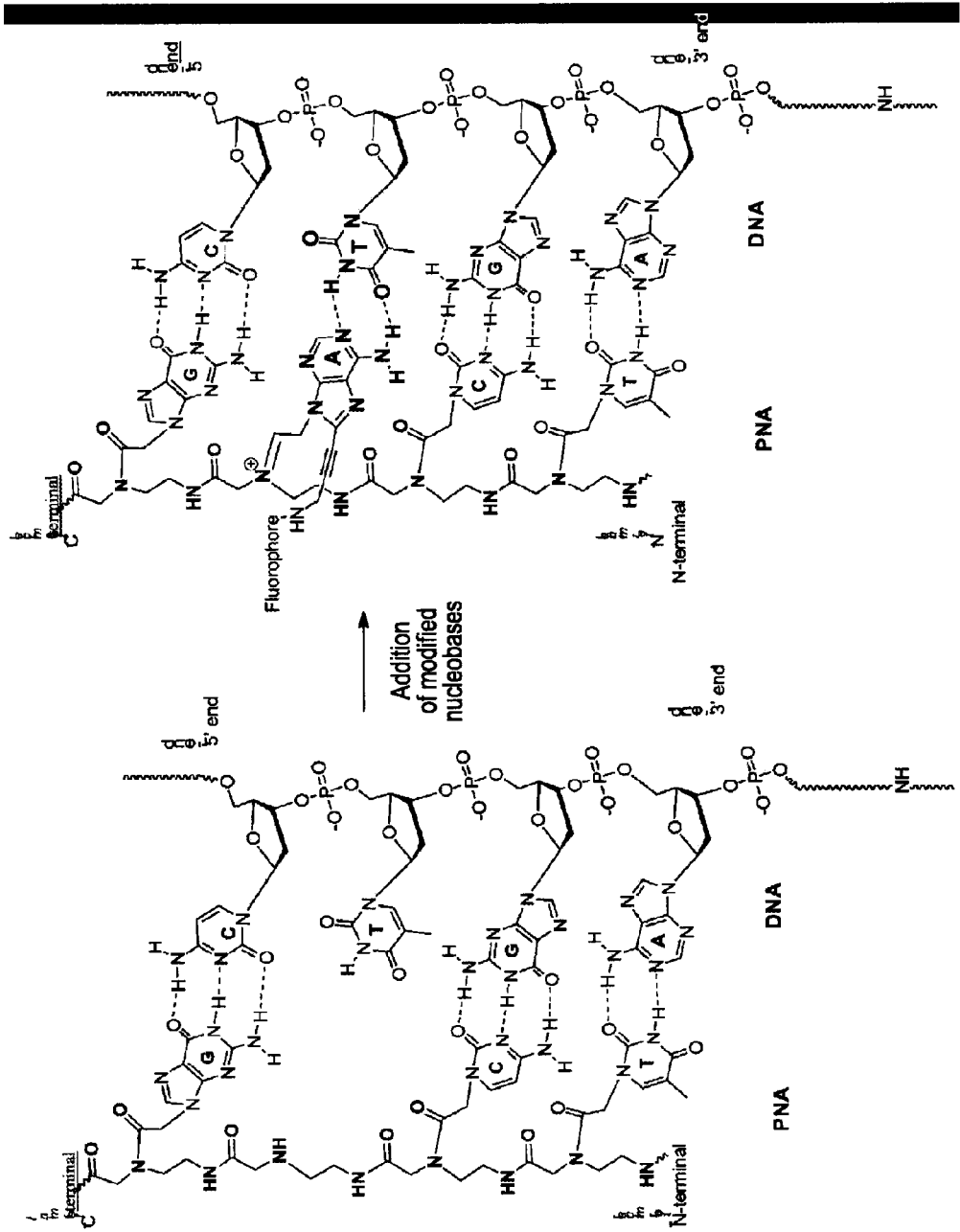

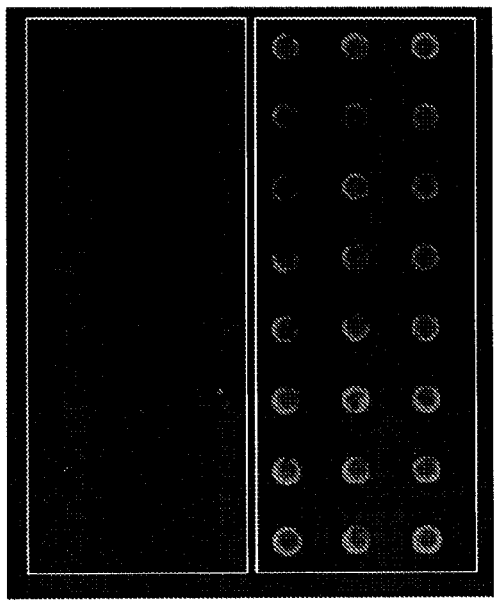 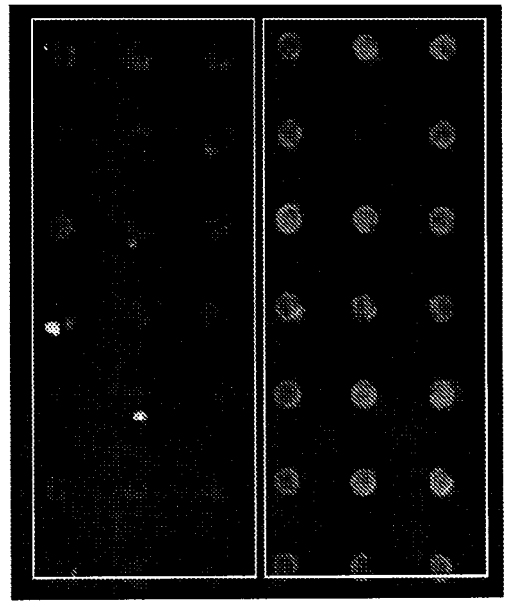
FIG. 14C  FIG. 14D
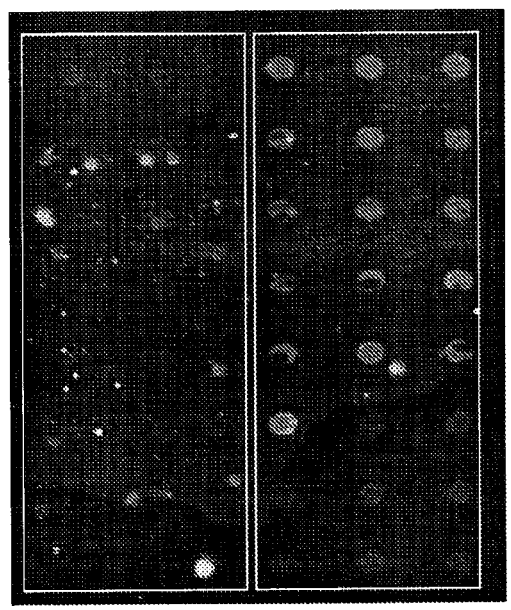
FIG. 14E

Nucleobases A, T, C, G

R= Dye, alkyl, acetamide ethyl
Z = H, Dye or Bromide

Z = at either 7 or 8
Y = C when Z at 7; N when Z at 8

US 8,716,457 B2

NUCLEOBASE CHARACTERISATION

RELATED APPLICATIONS

This application is a nationalization under 35 U.S.C. 371 of PCT/GB2008/003185, filed Sep. 19, 2008 and published as WO 2009/037473 A2 on Mar. 26, 2009, which claimed priority under 35 U.S.C. 119 to United Kingdom Application No.: 0718255.3, filed on Sep. 19, 2007, which applications and publication are incorporated herein by reference and made a part hereof in their entirety.

FIELD OF THE INVENTION

The present invention provides modified nucleobase compounds, modified nucleic acid mimetic compounds and various uses thereof. More specifically, the invention provides methods for nucleobase characterisation, SNP characterisation and nucleic acid sequencing.

BACKGROUND

Although two original methods that allowed DNA sequencing were published —the chemical approach of Maxim and Gilbert (A. M. Maxim and W. Gilbert, *PNAS*, 1977, 74, 560-564) and the enzyme based methods of Sanger (F. Sanger et al., *PNAS*, 1976, 5463-5467)—the dominant method currently used is based on Sanger's approach and so-called termination or dideoxy sequencing. This fundamental methodology is based on partial termination of a growing DNA chain to produce a ladder of labelled, terminated fragments, which require size separation for sequence analysis to be carried out. Obviously various improvements have been made since its inception, thus the labels have been converted from traditional radioactive nucleotides to fluorescent dyes, and capillaries (although often polymer filled) rather than flat gel electrophoresis are commonly used in high throughput applications. As a result there has been a massive drive to parallelism, such as the simultaneous running of 96 capillaries, the use of four dyes and analysis in a single channel, while enhancements in fluorescence sensitivity and more efficient polymerases have allowed longer sequencing runs. However, the fact that this method has inherent limitations can be seen by the colossal effort that has been required to sequence the human genome. A number of newer approaches have been reported over the past few years and really fall into three categories: (i). Sequencing by repetitive single base addition, (ii) Pyrosequencing and (iii) Restriction enzyme mediated cleavage or kinase ligation with deconvolution/decoding.

(i). Sequencing by repetitive single base addition. There are a number of reports in this area (Z. M. Li et al., *PNAS*, 2003, 100, 414-419; T. S. Seo et. al., *PNAS*, 2005, 102, 5926-5931; L. R. Bi et al., *J. Am. Chem. Soc.*, 2006, 128, 2542). This approach replies on the enzyme mediated addition of a single base to a growing, primed DNA strand. Single base addition is controlled by some modification of the triphosphate such that multiple additions are impossible. This can be a physical block on the nucleotide or a chemical block (e.g. an ester on the 3'OH group). This approach relies on fluorogenically labelled building blocks and typically following removal of the blocking group the fluorogenic reporter will also be cleaved, allowing another cycle of reactions to be entertained. There are a number of issues with this approach, thus the need for enzymes and complex triphosphates. There are also issues with cleavage and termination chemistries which need to be essentially quantitative in order to allow reasonable read lengths.

(ii). Pyrosequencing (P. Nyren et. al., *Anal. Biochem.*, 1996, 242, 84-89). In this approach a growing, primed DNA strand is treated with an enzyme and one of the four triphosphates. If the base is incorporated, pyrophosphate is liberated; if no incorporation then no pyrophosphate is generated. The pyrophosphate reacts with a sulfurylase which converts it in the presence of APS (adenosine-5'-phosphosulfate) to ATP. This is then treated with another enzyme (luciferase) to generate light. It is this light which is used to determine the addition or otherwise of a specific base to the growing DNA strand. If two or more bases of the same type are added at one time then more light is generated and this can be quantified. The process is then repeated with the next type of triphosphate allowing sequences to be generated. There are a number of issues, which include the fact that quantification of light emission is not always possible so longish stretches of single bases are essentially impossible to read (e.g. it is really impossible to distinguish between 14 or 15 bases of one type due to emission variations). This was the approach used in a recent paper describing sequencing from millions of beads arrayed in microwells (M. Margulies et al., *Nature*, 2005, 437, 376-380).

(iii). Restriction enzyme mediated cleavage or ligation with deconvolution/decoding (S. Brenner et al., *Nature Biotech.*, 2000, 18, 630-634). In this approach, sequences are cleaved with a restriction enzyme to give an overhanging sequence. These are then decoded using a series of 16 encoded adapters. The adapters are then cleaved themselves, which exposes the next set of bases to be decoded. A similar approach is possible using ligation. There are again a number of problems: multiple steps per deconvolution; labelled probes and a variety of enzymes are still needed; incomplete cleavage or unwanted cleavage etc. . . . This was the approach used by Brenner (S. Brenner et al., *Nature Biotech.*, 2000, 18, 630-634) as well as the approach used by Shendure and Church in their massive pareallel chip based sequencing (beads trapped in a polyacrylamide gel, J. Shendure et. al., *Science*, 2005, 308, 1728-1732 and R. D. Mitra et al., *PNAS*, 2003, 100, 5926-5931).

Single Nucleotide Polymorphisms: Another, but related area to sequencing is that of Single Nucleotide Polymorphisms (A-C. Syvanen et al., *Nature Genetics*, 2005, 37, S5-S10). Indeed SNP analysis can be viewed as sequencing a single base. Single nucleotide polymorphisms (SNPs) are on average found in every 300-1000 bases in humans and represent as much as 90% of all genetic variations between individuals. A SNP can constitute a genetic risk factor (or indeed advantage) to specific disease states as well as a host of physical features. SNP analysis methods are many and varied but generally consist of primer extension reactions using polymerases and fluorescently labelled triphosphates, although the methods of capture and analysis vary considerably. SNP analysis is a simple form of DNA sequencing in some respects, in that the identity of a single base is the major concern (although its context is of course crucial).

DNA Directed Ligations and Reactions. DNA and peptide nucleic acid (PNA) have been used in a number of ligation-based chemical approaches to synthesis (notably the work of D. R. Liu and O. Seitz-X. Li and D. R. Liu, *Angew. Chem. Int. Ed.*, 2004, 43, 4848-4870; S. Ficht et al., *ChemBioChem*, 2005, 6, 2098-2103). Non-enzymatic ligation has also been achieved in a DNA-DNA sense by Kool and Richert (N. Griesang et al., *Angew. Chem. Int. Ed.*, 2006, 45, 6144-6148 and ref therein (e.g. P. Hagenbuch et al., *Angew. Chem. Int.*

Ed. 2005, 44, 6588-6592))—who used classical nucleophilic addition chemistry to ligate DNA strands (3'-phosphothioate reacting with a 5'-iodothymidine) or monomers (e.g. 3' aminonucleotide reacting with an activated phosphate). The first approach could be used for color detection of RNA and DNA point mutations, however it requires large primers on both the nucleophile and electrophile. Richerts approach, although monomer based, required so called helper primers such that two primers spanning the single base-gap were required to direct incorporation. Liu used dynamic chemistry to make polymers of PNA using a DNA template (D. R. Liu et al. *J. Am. Chem. Soc.* 2003, 125, 13924-13925).

PNA have been previously used as genetic probes (see review by P. Paulosova and F. Pellestor *Ann. Genetique,* 2004, 47, 349-358) due to their accurate recognition of complementary DNA or RNA sequences, however due to their lack of recognition by polymerases their use as tool for genetic analysis has been very limited.

Dynamic chemistry: Over the past decade there has been intense activity in the area of dynamic (combinatorial) libraries (P. T. Corbett et al. *Chem. Rev.,* 2006, 106, 3652-3711; J. M. Lehn, *Chem. Eur. J,* 1999, 5, 2455-2463, O. Ramström and J. M. Lehn, *Nat. Rev. Drug Discov.* 2002 1, 26-36). A "dynamic library" can be prepared by mixing together in solution two complementary components, such as a selection of aldehydes and an amine, or diols and boronic acids, or thiols and disulfides in the presence of a template. Due to the dynamic equilibrium set up in the system (amine/aldehyde/ imine) the most strongly bound ligand will predominate and thus in essence the template "builds" and "concentrates" its own partner. Recently, Dawson et al. (*J. Am. Chem. Soc.,* 2006, 128, 15602-15603) showed that equilibrium kinetics of dynamic processes can also be accelerated by catalysts such as aniline.

As can be seen above, all the newer methods of DNA analysis (and the older methods) have a variety of issues and problems associated with their application, not least the use of enzymes and often expensive triphosphates.

The object of the present invention is to obviate or mitigate at least one of the aforementioned problems.

SUMMARY OF THE INVENTION

The invention described herein provides modified bases, modified nucleobases and DNA mimetic compounds which may be used in various nucleic acid sequencing and/or SNP characterisation methods. The invention provides clear advantages over the prior art as each of the methods described herein is chemical based and does not require the use of enzymes.

Accordingly, and in a first aspect, the present invention provides a modified base comprising a moiety capable of reversible covalent reactions and a detectable tag.

One of skill in the art will appreciate that bases (otherwise known as or referred to herein as "nucleobases") comprise purines and pyrimidines which include, for example the specific bases adenine, guanine, thymine, cytosine and uracil. As such, and in one embodiment, the present invention relates to modified adenine, guanine, thymine, cytosine and/or uracil bases. In addition, the present invention encompasses variants such as, for example, xanthine, hypoxanthine, isoguanine and uric acid.

It is to be understood that the term "modified base" may be taken to encompass bases/nucleobases comprising an alkyl chain further comprising functional groups capable of reversible covalent reactions. Preferably, the heterocycle of the bases may be modified so as to comprise the alkyl chain and functional groups. More specifically a heteroatom or carbon atom of the heterocycle may be modified to comprise the alkyl chain and functional groups.

It is to be understood that the functional groups capable of "reversible covalent reactions" may be, for example, groups comprising aldehydes and/or ketones and in one embodiment, the reversible covalent reactions may involve reactions between the aldehyde/ketone groups of the modified base and amines, hydrazide and hydrazides (A. Dirksen, et al., *J. Am. Chem. Soc.,* 2006, 128, 15602-15603), alkoxyamine (V. A. Polyakov et al., *J. Phys. Org. Chem.* 1999, 12, 357-363) or alcohols, diols and/or boronic acids (O. Abed et al. *Chem. Mater.,* 2006, 18, 1247-1260). In one embodiment, the group capable of a reversible covalent reaction is not an alcohol.

The term "detectable tag" may be taken to encompass tags or labels which are, for example, distinguishable from one another either optically or otherwise. Many such tags or labels are known to those skilled in this field but, by way of example, tags suitable for use in the present invention may include, for example, fluorescent or mass-tag compounds. More specifically, and in one embodiment, the modified bases/nucleobases of the present invention may comprise one or more detectable tag (such as, for example a fluorophore) selected from a group of tags having optically detectable dyes ranging from, for example, the blue to the far-red spectra. Examples of tags which may be suitable include, for example, dansyl, fluorescein, rhodamine, texas red, IAEDANS, cyanine dyes (Cy3, Cy3.5, Cy5, Cy5.5, Cy7), Bodipy dyes (Invitrogen) and/or Alexa Fluor dyes (Invitrogen). In one embodiment, the detectable tag is not ferrocene.

Suitable "mass-tag" compounds may include, for example, tags which comprise bromide moieties or other compounds, molecules or moieties capable of providing a clear isotopic pattern in mass-spectrometry techniques such as, for example, MALDI-TOF.

Accordingly, one of skill in the art will appreciate that any of the modified nucleobases described herein may be detected by, for example, fluorescent microscopy or mass spectrometry techniques such as MALDI-TOF or the like.

Advantageously, the heterocycle of each of the modified bases/nucleobases described herein may comprise a detectable tag linked, for example, at any number of positions through a heteroatom or a carbon atom. In one embodiment, the heteroatom may be modified so as to further comprise suitable spacer/carbon spacer moieties such as, for example an alkyne, alkenylene or alkynylene moiety which may be independently substituted with one or more of the detectable tags noted above. By way of example, the heteroatom and/or modified heteroatom of the heterocycle may comprise one or more fluorophore(s) (T. S. Seo et al., *PNAS,* 2004, 101, 5488-5493; Z. Li et al., *PNAS,* 2003, 100, 414-419; L. Thoresen et al., *Chem. Eur. J.* 2003, 9, 4603-4610) and/or mass tags i.e. bromide, chloride (C. Portal et al., *J. Comb. Chem.,* 2005, 7, 554-560). In one embodiment, the purine and/or pyrimidine heterocylces may be modified by, for example, cross coupling reactions using palladium catalysts (L. Thoresen et al., *Chem. Eur. J.* 2003, 9, 4603-4610; N. K. Garg et al. *Chem. Commun.,* 2005, 4551-4553).

Advantageously, each modified base/nucleobase may comprise a different detectable tag. In this way, the detectable tag may allow, for example, a modified adenine nucleobase to be distinguished from any other modified nucleobase.

In one embodiment, the present invention provides modified bases selected from the group consisting of:

Formula 1

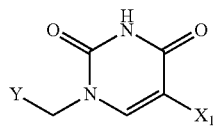

Formula 2

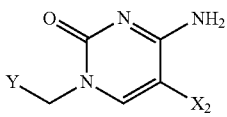

Formula 3

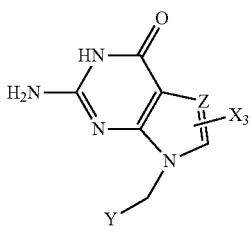

Formula 4

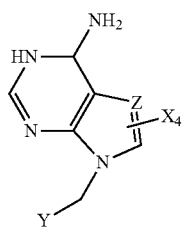

Wherein Y may comprise a functional group capable of reversible covalent reactions. Suitable functional groups may include, for example aldehydes, ketones and/or diols.

$X_1$-$X_4$ may be different detectable tags or spacer-tag combinations or hydrogen.

Z may be carbon, nitrogen, oxygen and sulphur.

In cases (iii) and (iv) above, X may be attached to the heterocycle either through Z, when Z is carbon, or through the carbon moiety at position 8.

In a further embodiment, the present invention provides modified bases selected from the group consisting of:

Formula 5

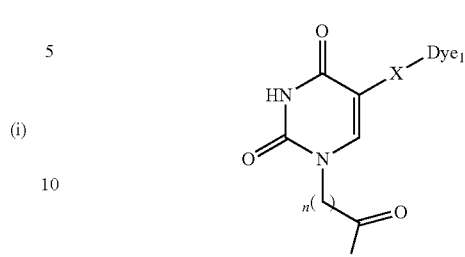

Formula 6

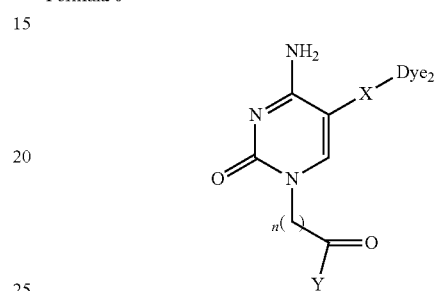

Formula 7

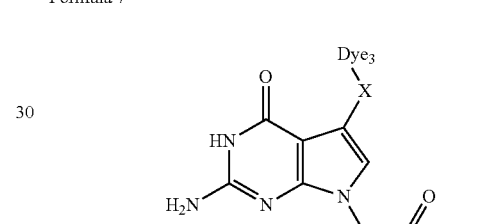

Formula 8

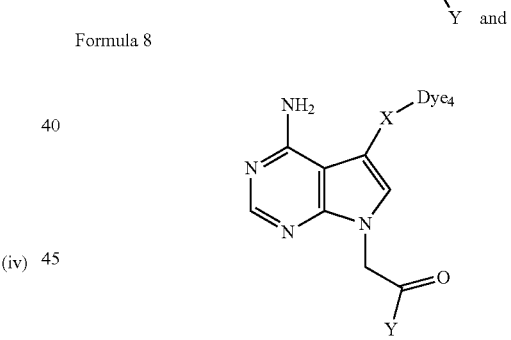

wherein X and Y may be hydrogen or a hydrocarbon chain, n equals 1, 2 or 3 and $Dye_1$-$Dye_4$ may be one or more of the detectable tags listed above. Preferably each of $Dye_1$-$Dye_4$ represents a different detectable tag such that, for example, the modified nucleobase of Formula 5 may be distinguished from those shown in Formula 6-8.

Peptide nucleic acid (PNA) is similar to the naturally occurring nucleic acids—deoxyribonucleic acid (DNA) and ribonucleic acid (RNA). While DNA and RNA possess a deoxyribose or ribose sugar backbone respectively, the backbone of PNA comprises repeating N-(2-aminoethyl)-glycine units which are linked by peptide bonds. The various pyrimidine and/or purine bases (or nucleobases) of PNA, are linked to the peptide backbone by amide bond formation. One of skill in the art will understand that a single nucleobase linked via an amide bond to a single N-(2-aminoethyl)-glycine unit may be described as a PNA monomer, but other PNA's include for example, those containing modified aminoethyl-glycine backbones, such as, for example, pyrrolidine-based (R. J. Worthington et al. *Org. Biomol. Chem.,* 2007, 5, 249-259) and indol-based DNA mimics (Formula 9). One skilled in the art will recognise other suitable oligomers.

Formula 9

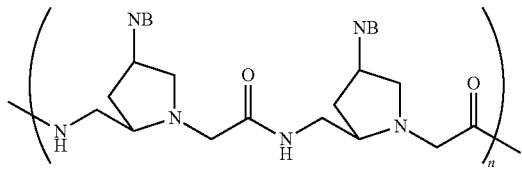

In a second aspect, the present invention provides modified PNA monomers having the following general formula:

Formula 10A

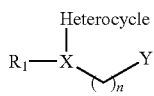

wherein, "heterocycle" is a modified base (such as, for example, cytosine, adenine, guanine or thymine/uracil)) which may comprise a detectable tag, n equals 1, 2 or 3 and further wherein, X represents a way of linkage between the heterocycle and the backbone comprising $R_1$ and Y. $R_1$ represents a group capable of reversible covalent reactions. By way of example, $R_1$ may comprise groups such as an amine, a hydrazide, an alkoxymine, a boronic acid, a diol and/or a thiol.

Y, may be a functional group capable of reversible covalent reactions such as, for example, an aldehyde, a ketone, a diol, a boronic acid and a thiol.

In a further embodiment, the present invention provides modified PNA monomers having the following general formula:

Formula 10

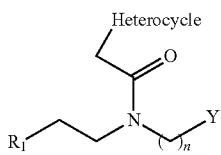

wherein, "heterocycle" is a modified base (such as, for example, cytosine, adenine, guanine or thymine/uracil) which may comprise a detectable tag as described above, n equals 1, 2 or 3 and further wherein, $R_1$ represents a group capable of reversible covalent reactions. By way of example, $R_1$ may comprise groups such as an amine, a hydrazide, an alkoxymine, a boronic acid, a diol and/or a thiol.

Y may be a functional group capable of reversible covalent reactions such as, for example, an aldehyde, a ketone, a diol, a boronic acid and a thiol.

It is to be understood that $R_1$ may be derivatised to comprise a protecting group or optionally a protecting group comprising (for example, covalently bound to) one or more of the detectable tags described above.

Suitable protecting groups for use in further derivatising $R_1$ may include, for example, protecting groups such as acetyl, N-[1-(4,4-dimethyl-2,6-dioxocyclohex-1-ylidene)ethyl] (Dde), fluorenylmethoxycarbonyl (Fmoc), trityl groups, disulfide (Ardec (aryldithioethyloxycarbonyl)) light cleavage protecting group (nitroveratyl based), butyloxycarbonyl (Boc), benzyloxycarbonyl (Cbz), trifluoroacetyl (Tfa), phthalimide, benzyl, allyloxycarbonyl (Alloc), toluensulfonyl (Ts), methoxymethyl ether (MOM), tetrahydropyranyl ether (THP), allyl ether, butyl ether, benzylidene acetal (Green, Wiley-Interscience, New York, 1999).

In one embodiment, the modified PNA monomers may be selected from the group consisting of:

Formula 11

(i)

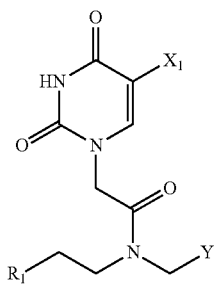

Formula 12

(ii)

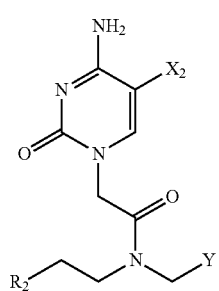

Formula 13

(iii)

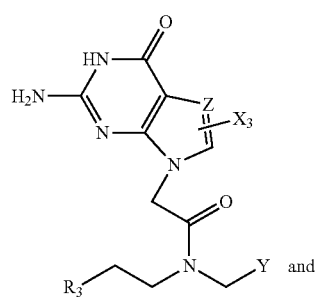

and

Formula 14

(iv)

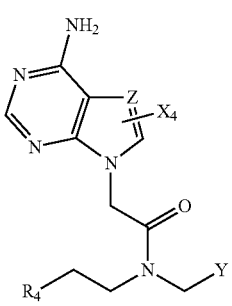

wherein R₁-R₄ may comprise a group capable of reversible covalent reactions (see above) optionally protected with a protecting group (as described above). Additionally, or alternatively, R₁-R₄ may comprise a protecting group which further comprises (for example covalently bound to) one or more of the detectable tags described herein.

X₁-X₄ may be one or more of the detectable tags described herein and may be linked to the heterocycle at any number of positions through a heteroatom or a carbon atom. In one embodiment, the heteroatom may be modified so as to further comprise suitable spacer/carbon spacer moieties such as, for example, an alkyne, alkenylene or alkynylene moiety, which may be independently substituted with one or more of the detectable tags noted above.

X₁-X₄ is a detectable tag linked to the heterocycles by a cleavable linker or a hydrogen. Z may be carbon, nitrogen, oxygen and sulphur and in cases (iii) and (iv) above, X may be linked to the heterocycle either through Z, when Z is carbon, or through the carbon at position 8.

Y may be a functional group capable of reversible covalent reactions such as, for example, an aldehyde, a ketone, a diol, a boronic acid and a thiol.

In a further embodiment, the present invention provides modified PNA monomers selected from the group consisting of:

Formula 15

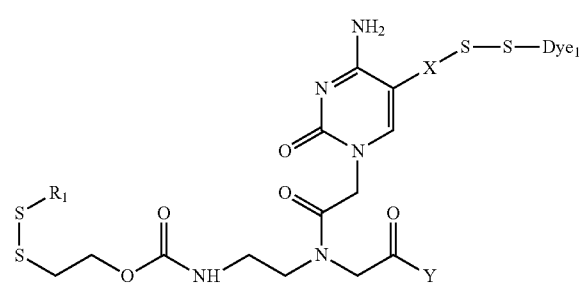

(i)

Formula 16

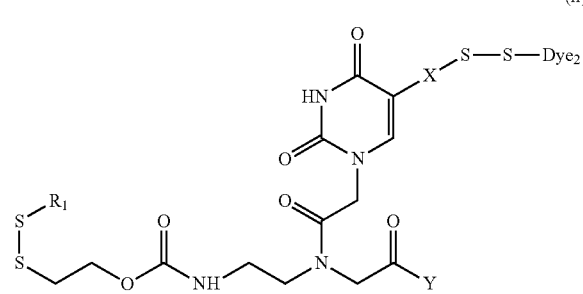

(ii)

Formula 17

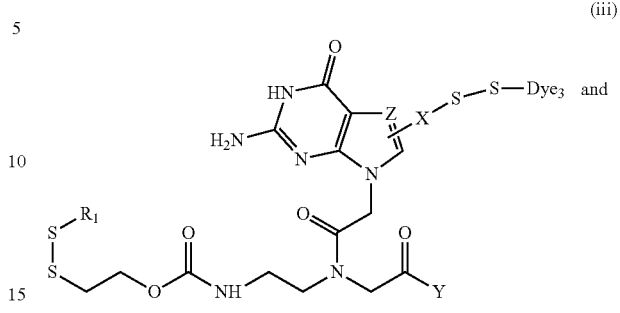

(iii)

Formula 18

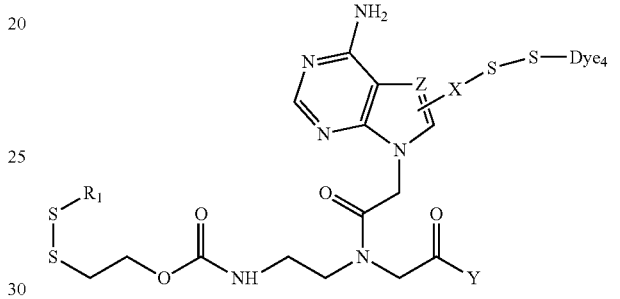

(iv)

wherein R₁ may be a hydrocarbon chain, and aryl ring, X may be a hydrocarbon chain and Y may be a hydrocarbon chain or hydrogen.

In a further embodiment, the present invention provides modified bases selected from the group consisting of:

Formula 19

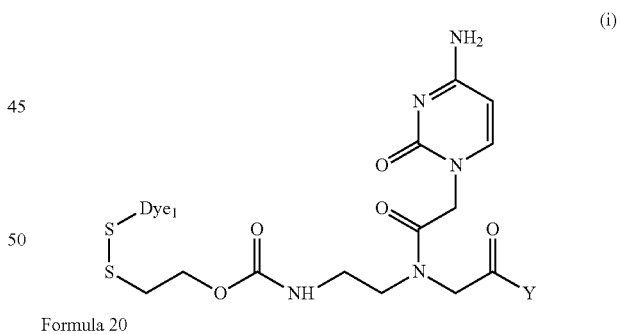

(i)

Formula 20

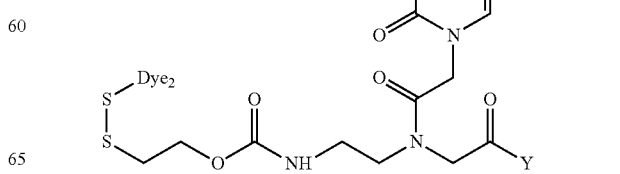

(ii)

Formula 21

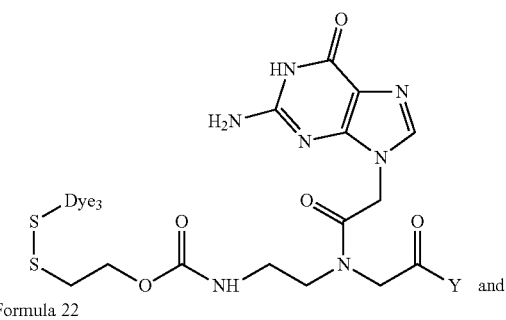

and

Formula 22

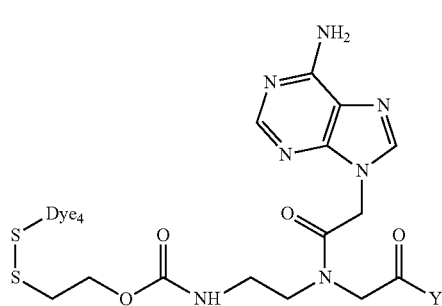

wherein Y may be a hydrogen or a hydrocarbon chain.

One of skill in the art will appreciate that in addition to providing PNA monomers, the present invention may relate to PNA dimers or trimers. The term "PNA dimer" according to this invention should be understood as relating to two (or three in the case of a PNA "trimer") PNA monomers which are covalently linked. In one embodiment, a PNA dimer may comprise at least one nucleobase modified to include any of the detectable tags described herein. In other embodiments, the PNA dimers may comprise at their N or C terminal ends any one of the detectable tags described herein.

In instances where the N or C-terminal end of the PNA dimer is modified to include a detectable tag, the other of the N or C terminal end may include a moiety capable of reversible covalent reactions. As such, in one embodiment, the present invention provides PNA dimers (or trimers) comprising at the N-terminal end a detectable tag and at the C-terminal end, a moiety capable of reversible covalent reactions. Furthermore, in certain embodiments, at least one of the nucleobases of the PNA monomers may further comprise a detectable tag.

Exemplary methods of producing PNA dimers (or trimers) and examples of specific forms of PNA dimer encompassed by this invention are described in more detail below.

The present invention also concerns PNA oligomers and one of skill in the art will readily understand that the term "oligomer" may be taken to refer to a molecule comprising at least two PNA monomers linked by, for example, a peptide bond. The invention also concerns other DNA mimics as noted above.

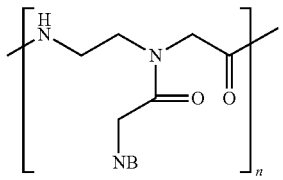

Formula 23 wherein NB is a nucleobase (for example a modified nucleobase according to the present invention) and n is at least 2.

In view of the above, one of skill will appreciate that a PNA oligomer typically comprises a continuous peptide backbone with each secondary amine of the peptide backbone being further derivatised to comprise a nucleobase (such as the modified nucleobases described above). In a further embodiment, the present invention may provide a PNA oligomer in which some of the secondary amines of the continuous peptide backbone are not derivatised to comprise a nucleobase and hence are left uncoupled. These oligomers may be referred to as oligomers comprising "blank positions". Formula 24 below provides an example of a PNA monomer comprising a blank position (i.e. secondary amine No: 3 is not derivatised to comprise a nucleobase (NB))

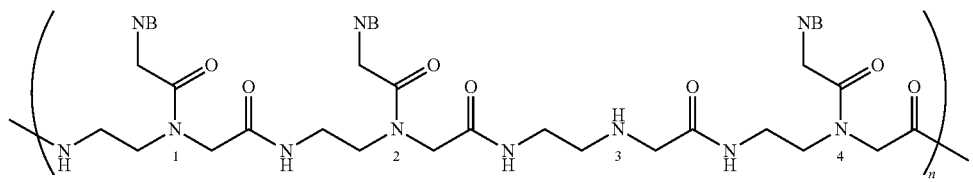

Formula 24

In one embodiment, PNA oligomers of the invention may further comprise, at either the N or C-terminal positions, a group capable of reversible covalent reactions. For example, the N-terminal position may comprise a free amine group, aldehyde/ketone hydrazide, hydrazine, alkoxyamine, alcohols, diols and/or boronic acids and the C-terminal position may comprise a group capable of forming a reversible covalent reaction with the group at the N-terminal position. In one embodiment, either of the N-terminal and/or C-terminal positions may be derivatised so as to further comprise a protecting group (as described above).

The PNA oligomers for use in the methods described herein may be synthesised using N-2aminoethyl-glycine units protected with orthogonal protecting groups. Such units may have the following general formula:

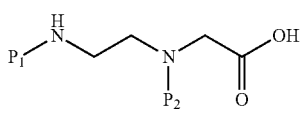

Formula 25 wherein $P_1$ and $P_2$ may be disulfide (Ardec (aryldithioethyloxycarbonyl)), light cleavage protecting group (nitroveratyl based), butyloxycarbonyl (Boc), benzyloxycarbonyl (Cbz), trifluoroacetyl (Tfa), phthalimide, benzyl, allyloxycarbonyl (Alloc) N-[1-(4,4-dimethyl-2,6-dioxocyclohex-1-ylidene)ethyl] (Dde), fluorenylmethoxycarbonyl (Fmoc), t-butoxycarbonyl (Boc) and trityl groups (Green, Wiley-Interscience, New York, 1999).

The PNA oligomers described above may find particular application in genetic analysis methods.

As such, in a third aspect, the present invention provides a use for one or more of the modified bases/nucleobases provided by the first aspect of the present invention and/or the PNA monomers/oligomers described herein, in genetic analysis methods. It is to be understood that "genetic analysis" may include, for example, the characterisation, identification and/or sequencing of nucleobases of nucleic acids. In one embodiment, the methods may be used to characterise single nucleotide polymorphisms and/or to sequencing nucleic acids.

One of skill in the art will be familiar with the term "single nucleotide polymorphism" or "SNP". Briefly, a "SNP" represents a form of variation in a genome wherein a particular nucleotide of the genome varies between members of a population. By way of example, a SNP may comprise two alleles (i.e. one of two possible nucleotides at a particular locus)—and, in such cases some of the individuals within a population may carry one SNP allele at a particular locus while others may carry the other allele at the same locus.

Accordingly, the phrase "characterising a nucleobase" may be taken to encompass the act of identifying or determining a particular nucleobase of a nucleic acid sequence—in other words, identifying which nucleobase a particular nucleotide comprises. In instances where the methods are used to characterise a SNP, the term "characterise" may be taken to encompass the act of determining which particular SNP allele (or nucleobase) is present in a particular nucleic acid sequence.

Thus, in a fourth aspect, the present invention provides a method of characterising a nucleotide in a nucleic acid sequence, said method comprising the steps of:

(a) contacting a nucleic acid with a peptide nucleic acid (PNA) oligomer capable of hybridising to a portion of the nucleic acid and lacking a nucleobase complementary to a nucleobase of the nucleic acid, to form a nucleic acid/PNA duplex; and (b) contacting the nucleic acid/PNA duplex with modified bases according to the first aspect of the invention;

wherein the modified nucleobase which integrates with the nucleic acid/PNA duplex is complementary to the nucleobase of the nucleic acid, the nucleotide being characterised by means of the detectable tag of the PNA monomer.

One of skill in the art will appreciate that the part of the PNA oligomer which lacks a base complementary to a nucleobase of the nucleic acid sequence, may present a moiety, for example a secondary amine, capable of reacting reversibly with a moiety of the modified bases described above. As such, upon contact with the nucleic acid/PNA duplex, a modified base which is complementary (or matched) to a nucleobase of the nucleic acid, may be incorporated into the nucleic acid/PNA duplex by the formation of, for example: (i) a reversible iminium species between the secondary amine of the PNA oligomer and the reacting moiety (aldehyde group) of the modified nucleobase and (ii) the formation of hydrogen bonds between the modified nucleobase and the nucleobase of the nucleic acid.

In one embodiment, the method may comprise the further step of trapping the base integrated with the nucleic acid/PNA duplex and complementary to (i.e. paired with) the nucleotide of the nucleic acid. For example, the reversible reaction between the secondary amine of the PNA oligomer and the group capable of reversible covalent reactions of the modified nucleobase may be stopped. For example, iminium species may be reduced to give rise to stable tertiary amines using reducing agents such as sodium cyanoborohydride.

It is to be understood that the phrase "capable of hybridising to a portion of the nucleic acid sequence" should be taken to mean that the PNA oligomer is complementary to, or shares a certain degree of homology with, a portion of the nucleic acid sequence.

The skilled artisan will readily understand that by means of the detectable tag present on each of the modified nucleobases contacted with the nucleic acid/PNA duplex, it may be possible to detect which modified base has been incorporated into the nucleic acid/PNA duplex. As such, characterisation of the nucleotide of the nucleic acid may easily be achieved. For example, if the modified nucleobase found to have integrated with the nucleic acid/PNA duplex comprises a tag which indicates that it comprises a thymine nucleobase, in accordance with standard complementary base pairing, the nucleotide of the nucleic acid must comprise an adenine nucleobase.

Without wishing to be bound by theory, the integration of a modified nucleobase which is complementary to a nucleobase of a nucleic acid, may represent an example of a dynamic selection process which relates to the various interaction strengths of the complementary (matched) and un-matched nucleobases, as well as the relative concentrations of the four modified nucleobases and may be controlled by changes in the buffer concentrations, pH, temperature and also uses of different catalysts. Dynamic selection processes are well known to one of skill in this field and encompass systems in which a number of complementary components are mixed together in the presence of a template (J. M. Lehn, *Nat. Rev. Drug Disc.*, 2002 1, 26-36). Due to the dynamic equilibrium set up in such a system, the most strongly bound ligand will predominate and thus the template "builds" or selects from the various component parts added, its own "ligand" or "partner".

Advantageously, the nucleic acid/PNA duplex is contacted with each of the modified nucleobases described above. Typically, the nucleic acid/PNA duplex will be contacted with modified nucleobases comprising nucleobases complementary to each of the nucleobases likely present in the nucleic acid sample. For example, and in one embodiment, the nucleic acid/PNA duplex may be contacted with the modified adenosine, guanine, cytosine and thymine bases described above. Furthermore, by ensuring that each type of modified bases used in the methods described herein comprises a tag which allows it to be separately distinguished from the other modified nucleobases, characterisation of a nucleotide in a nucleic acid sample may be readily achieved.

While the methods described herein may be conducted in solution, it may be advantageous to immobilise or otherwise bind the nucleic acid or PNA oligomer to some form of support substrate, preferably a solid support substrate. In one embodiment, the support substrate may comprise glass, nitrocellulose, cellulose, plastic, agarose, beads, a metal (such as for example gold) or the like. In the case of beads, sizes of approximately 1 nm to about 2 mm are preferred.

In a fifth aspect, the present invention provides an alternate method of characterising a nucleotide of a nucleic acid. As stated, the term "characterise" encompasses the act of identifying a particular nucleobase of a nucleotide. It is to be noted that all of the definitions provided above also to apply to this aspect of the invention. The method according to the fifth aspect comprises the step of:

(a) hybridising a nucleic acid sequence with a PNA oligomer complementary to a portion of the nucleic acid sequence upstream of the nucleotide to be characterised and further comprising a functional group capable of reversible covalent reactions, to form a nucleic acid/PNA duplex; and (b) contacting the nucleic acid/PNA duplex with modified PNA monomers according to the second aspect of the invention;

wherein the modified PNA monomer which integrates with the nucleic acid/PNA duplex is complementary to the nucleobase of the nucleotide, said nucleotide being characterised by means of the detectable tag of the PNA monomer.

Preferably, the PNA oligomer hybridises with, or is complementary to, a sequence of the nucleic acid which lies immediately upstream of the nucleotide to be characterised. In other words the PNA oligomer may hybridise with or bind to a nucleic acid sequence at a position 3' to the nucleotide of the nucleic acid such that the terminal (or $N\text{-}_{end}$) residue of the PNA oligomer, lies immediately adjacent the nucleotide to be characterised.

Advantageously, the nucleic acid/PNA duplex is contacted with modified PNA monomers (such as those provided by the second aspect of the invention) comprising nucleobases complementary to each of the nucleobases likely present in the nucleic acid sample. For example, and in one embodiment, the nucleic acid/PNA duplex may be contacted with modified PNA monomers comprising the adenosine, guanine, cytosine and thymine nucleobases described above.

One of skill in the art will understand that when the PNA monomers are contacted with the nucleic acid/PNA duplex, the PNA monomer comprising the modified nucleobases complementary to the nucleobase of the nucleic acid will, by dynamic selection (as described above), become integrated into the nucleic acid/PNA duplex.

The methods described herein and particularly the method provided by the fifth aspect of this invention may utilise the PNA dimers provided by this invention. In such cases, rather than using the PNA monomers as described in, for example, step (b) above, the method provided by the fifth aspect may utilise the PNA dimers (or trimers) described herein. Furthermore, the PNA oligomer hybridized to the nucleic acid sequence comprising the nucleotide to be characterised, may be hybridized in such a way that, while upstream of the nucleotide to be characterised, the terminal (or $N\text{-}_{end}$) residue of the PNA dimer lies adjacent a nucleotide which is itself immediately adjacent the nucleotide to be characterised. In this way, in order to correctly hybridise with the nucleic acid strand containing the nucleotide to be characterised, the PNA dimer must comprise two complementary nucleobases—one complementary to the nucleotide to be characterised and the other complementary to the nucleotide immediately upstream thereof.

One of skill will appreciate that when using PNA trimers rather than PNA monomers or dimers, the PNA oligomer may be hybrised to the nucleic acid sequence comprising the nucleotide to be characterised, such that there are two nucleotides of the nucleic acid sequences between the N-terminal end of the PNA oligomer and the nucleotide to be sequenced. In this way, a correctly integrating PNA trimer must possess three complementary nucleobases; two complementary to the nucleotides immediately upstream of the nucleotide to be characterised and one complementary to the nucleotide to be characterised.

In one embodiment, the method provided by the fifth aspect of this invention may further comprise the step of trapping the modified PNA monomer (or PNA dimer/trimer) comprising the nucleobase complementary to the nucleobase of the nucleic acid, by for example, stopping the reversible reaction. For example, imine species may be reduced in a process known as reductive amination using redacting agents such as sodium cyanoborohydride.

Advantageously, since each of the modified PNA monomers (or PNA dimers or trimers) is labelled with at least one detectable tag which is distinguishable from the detectable tags on other types of PNA monomer (dimer or trimer), detection of the specific monomer (dimer or trimer) which has integrated may be easily achieved.

One of skill will readily understand that where PNA dimers are used, there are 16 possible combinations of the four standard nucleotides (A, G, T and C) which must be taken into consideration. As such, when using PNA dimers, the methods described herein may require the addition of all 16 possible PNA dimers. Similarly, when using PNA trimers, there are 64 possible combinations of the four standard nucleotides—as such, when using PNA trimers, the methods described herein may require the addition of all 64 PNA trimers.

As stated, it is to be understood that while each of the above-described methods has been described with reference to the characterisation of a particular nucleobase/nucleotide of a nucleic acid sequence, the methods may also permit the user to characterise a SNP present in a nucleic acid sample. For example, if a SNP is known to occur at a particular locus within a gene, by designing PNA oligomers which hybridise either side of the SNP locus or immediately upstream of the SNP locus (as described above) it may be possible to characterise the SNP (i.e. identify which particular SNP allele is present at that locus). Such methods may be particularly useful in detecting mutations associated which particular genetic disorders.

In a sixth aspect, the present invention provides a method of sequencing a nucleic acid, said method comprising the steps of:

(a) hybridising a nucleic acid sequence with a PNA oligomer capable of hybridising to a portion of said nucleic acid sequence and having at its N-terminal position a functional group capable of interacting with a PNA monomer according to the second aspect of the invention, under conditions which permit the formation of a nucleic acid/PNA duplex; and (b) contacting the nucleic acid/PNA duplex with PNA monomers according to the second aspect of the invention;

wherein the PNA monomers which integrate with the nucleic acid/PNA duplex is complementary to a nucleobase of the nucleic acid sequence which may subsequently be identified by means of the detectable tag of the PNA monomer.

Since each PNA monomer may be labelled with a detectable tag which is distinguishable from the detectable tags of PNA monomers comprising another nucleobases, by detecting the tag of the PNA monomer which has integrated into or with the nucleic acid/PNA duplex, it may be possible to sequence a nucleic acid.

In addition, and as has been described above, the method provided by the sixth aspect of this invention may, rather than using PNA monomers in step (b), use the PNA dimers and/or trimers provided by this invention.

Preferably, each of the PNA monomers (or dimers or trimers) contacted with the nucleic acid/PNA duplex may comprise, at its N-terminal position a blocking group (as described above). Such PNA monomers (or dimers or trimers) are referred to hereinafter as "blocked PNA monomers (dimers/trimers)". Methods which use blocked PNA monomers (dimers/trimers) are particularly advantageous as only one PNA monomer can integrate with a nucleic acid/PNA duplex at a time. In order for further PNA monomers (dimers or trimers) to be subsequently integrated, the blocking group of the integrated PNA monomer (dimer or trimer) must first be removed (optionally together with any detectable tag). In this way, prior to the addition of a further PNA monomer (dimer or trimer: blocked or otherwise), the detectable tag of the integrated modified nucleobase may be identified and the corresponding nucleobase of the nucleic acid determined.

The techniques which may be used to remove the protecting group (together with any tag present) are known to one of skill in the art and may include, for example basic-based cleavage, acidic-based cleavage, disulfide reduction, metal-based catalytic reactions, light-based cleavage reactions (Green, Wiley-Interscience, New York, 1999).

Removal of the protecting group and any tag present on the integrated modified nucleobases, may expose or yield a moiety (such as a free amine; group, aldehyde/ketone, hydrazide, hydrazine, alkoxyamine, alcohols, diols and/or boronic acids capable of reacting reversibly with another PNA monomer. In addition, the method may comprise the further step of trapping the integrated PNA monomer so as to prevent further reversible reactions. For example, reduction of the imine species with sodium cyanoborohydride and further trapping of the generated secondary amine by, for example, an amidation step using acetylchloride. Since each modified nucleobase to integrate with the nucleic acid/PNA duplex binds to a complementary nucleobase of the nucleic acid, the methods described herein render it is possible to sequentially determine the sequence of a nucleic acid.

Each of the methods described herein offers many advantages over the prior art. In particular, no enzymes are needed and no labelled triphosphates are necessary—only labelled PNA monomers, dimers or trimers are used. In addition, there is no need to use current fluorophore attachment strategies as existing strategies, such as for example the use of alkynes, are only used due to enzyme requirements (Q. Meng et al., *J. Org. Chem.*, 2006, 71, 3248-3252).

One of skill in this field will appreciate that any of the methods provided by this invention, and in particular the methods provided by the fourth, fifth and sixth aspects of this invention may require the use of microarray technology. For example, the nucleic acid comprising the nucleotide to be characterised may be immobilised on to some form of suitable substrate using, for example, a micro printing system or the like. In this way, a large number of different nucleic acids can be immobilised on to substrates in discrete areas such.

In other embodiments, the nucleic acids comprising nucleotides to be characterised may be held in solutions with the other components i.e. the PNA oligomers, modified nucleobases etc. being added in solution also.

In further embodiments, the nucleic acids comprising nucleotides to be characterised may be immobilised on to substrates such as, for example, gold surfaces suitable for mass-spectrometry analysis.

In a seventh aspect of this invention, there is provided a kit comprising the reagents and components required for the methods provided by the fourth, fifth and sixth aspects of this invention. In one embodiment, the kit may provide reagents and components useful in methods for characterising a nucleotide of a nucleic acid and/or for sequencing a nucleic acid, said kit comprising components selected from the group consisting of:

(a) a peptide nucleic acid (PNA) oligomer capable of hybridising to a portion of a nucleic acid and lacking a nucleobase complementary to that of the nucleotide to be characterised;

(b) modified nucleobases according to the present invention;

(c) PNA monomers, dimers, trimers and/or oligomers as described herein; and (d) a PNA oligomer complementary to a portion of the nucleic acid sequence upstream of the nucleotide to be characterised and further comprising a functional group capable of reversible covalent reactions.

One of skill in the art will appreciate that, while the present invention has been described with reference to the DNA mimetic PNA, other DNA mimics could also be used provided they allow dynamic incorporation of the nucleobases. Such alternate mimetic include those disclosed by R. J. Worthington et al., *Org. Biomol. Chem.*, 2007, 5, 249-259. In addition, it may be possible to use modified DNA dimers, trimers and/or oligomers in the methods provided by the fourth, fifth, sixth and seventh aspects of this invention. More specifically, those steps which require the use of a PNA oligomer capable of hybridising to a nucleic acid sequence to be sequenced or comprising a nucleotide to be characterised may, in alternative embodiments utilise DNA dimers, trimers and/or oligomers modified to include the requisite functional groups capable of reversible reactions and/or blank positions corresponding to nucleotides to be characterised.

DETAILED DESCRIPTION

The present invention will now be described in detail and with reference to the following Figures which show:

FIG. 1: Structures of PNA and DNA showing PNA-DNA hybridisation.

Figure 2:
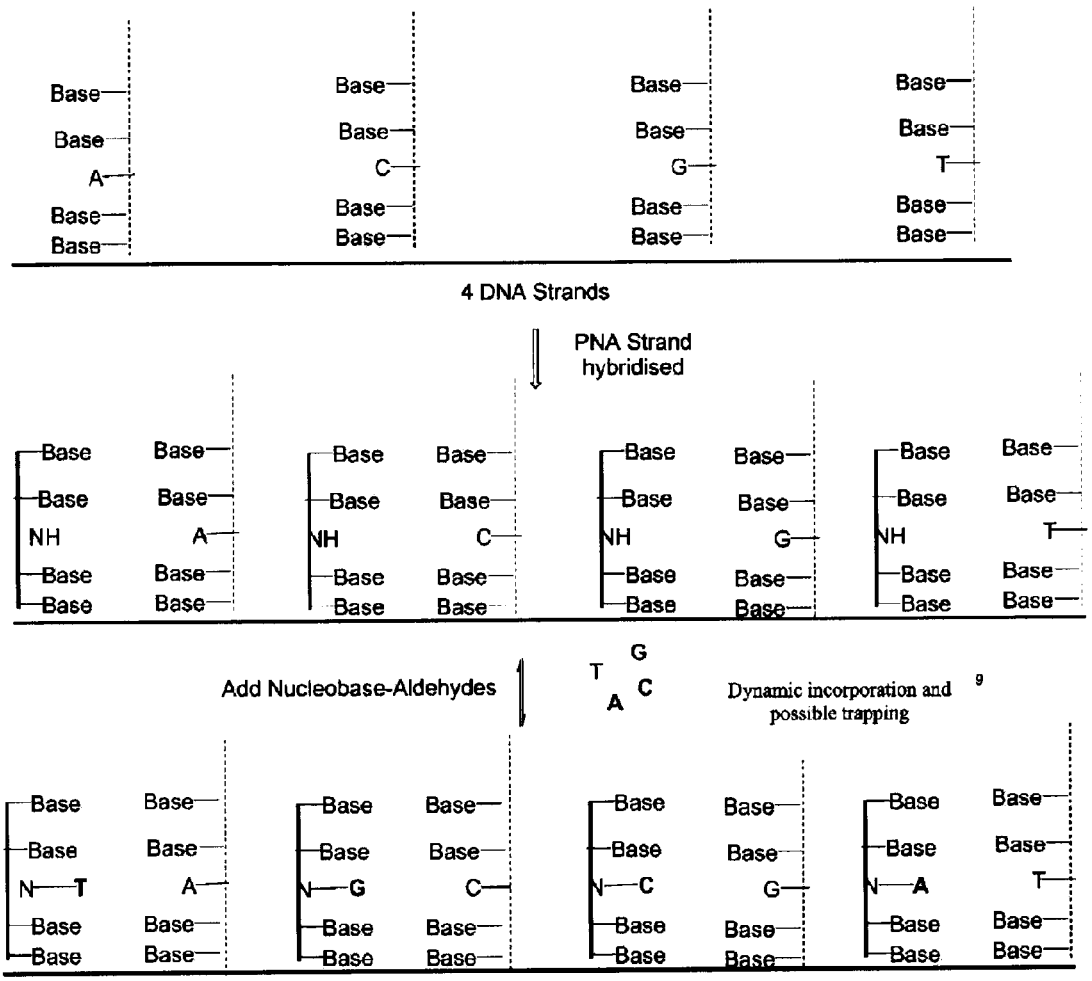

FIG. 2: Dynamic-based SNP analysis. A complementary PNA sequence lacking a base opposite a SNP location, is hybridised to a nucleic acid sequence comprising a SNP, to form a nucleic acid/PNA duplex. By dynamic attachment, the base complementary to the SNP nucleotide integrates with the nucleic acid/PNA duplex. Each modified base may be labelled with a specific tag which may be a fluorophore (see FIG. 1)

Figure 3:
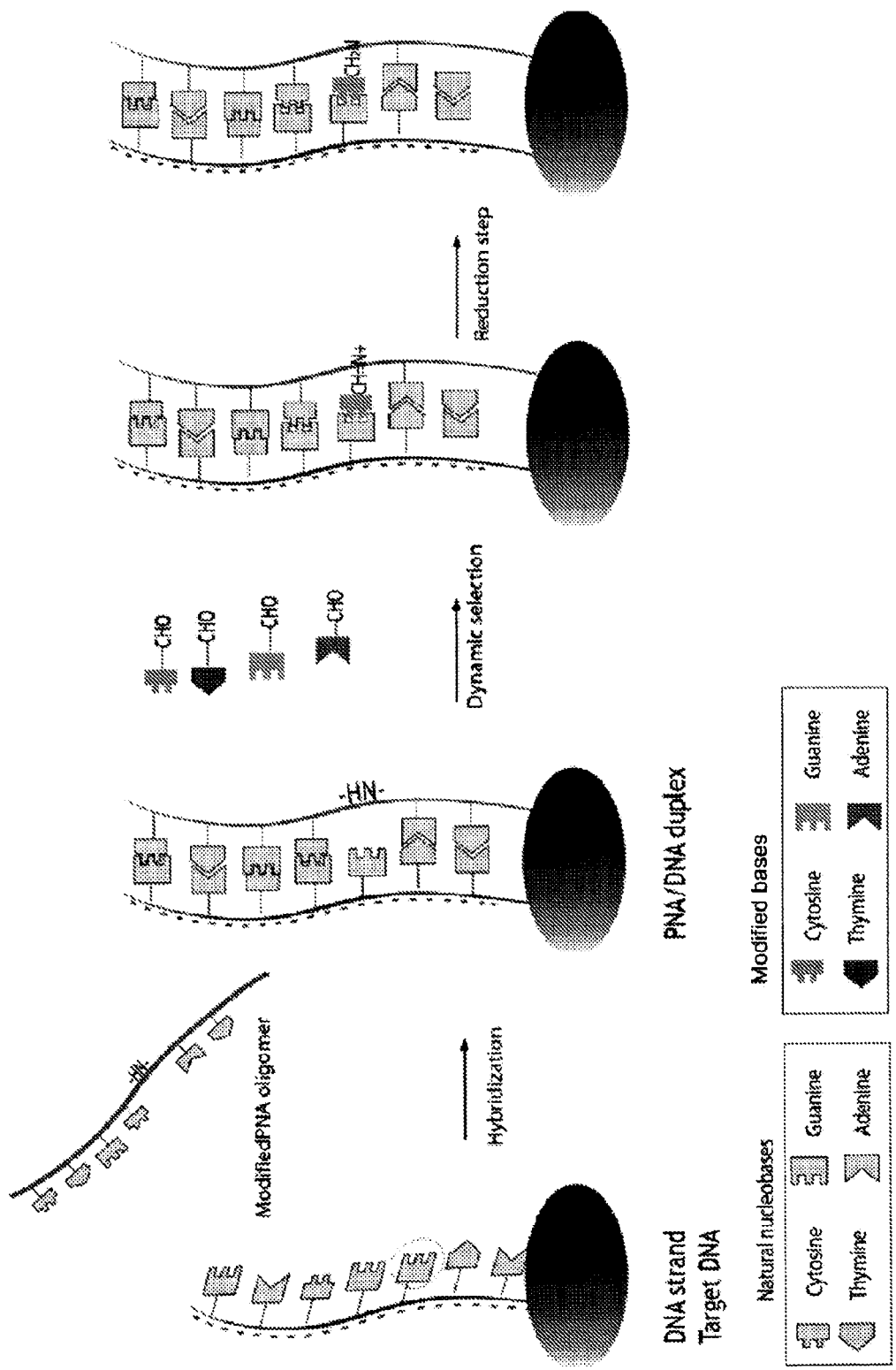

FIG. 3: Illustration of the dynamic-based SNP analysis shown in FIG. 2.

Figure 4:
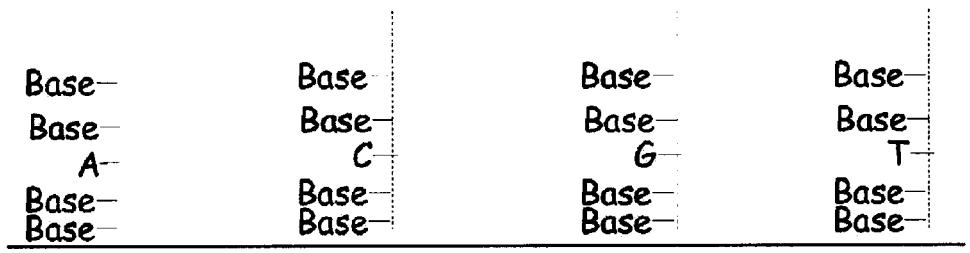
Figure 4:
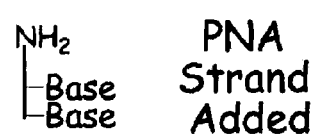
Figure 4:
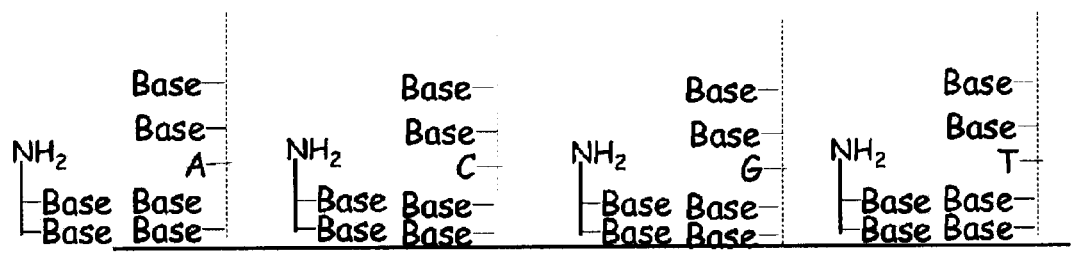
Figure 4:
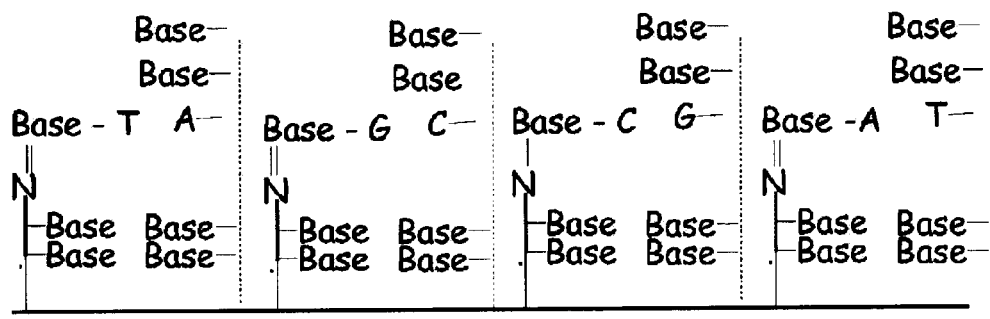

FIG. 4: Alternative method for dynamic-based SNP analysis—DNA oligomers are hybridised with complementary PNA oligomers having free amino groups at the N-terminus which permit the dynamic attachment of the base complementary to the SNP nucleobase.

Figure 5:
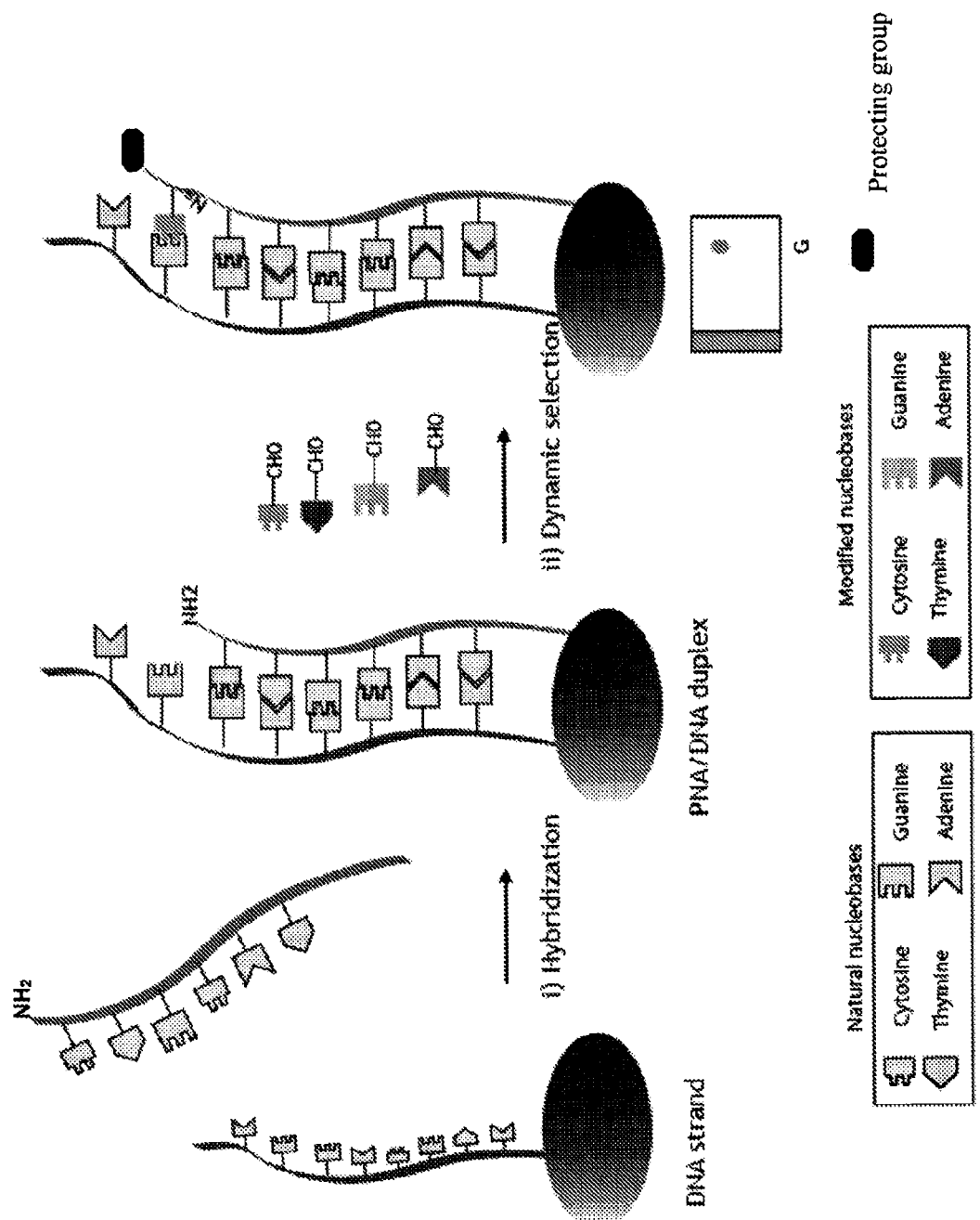

FIG. 5: Illustration of the dynamic-based SNP analysis shown in FIG. 4.

Figure 6:
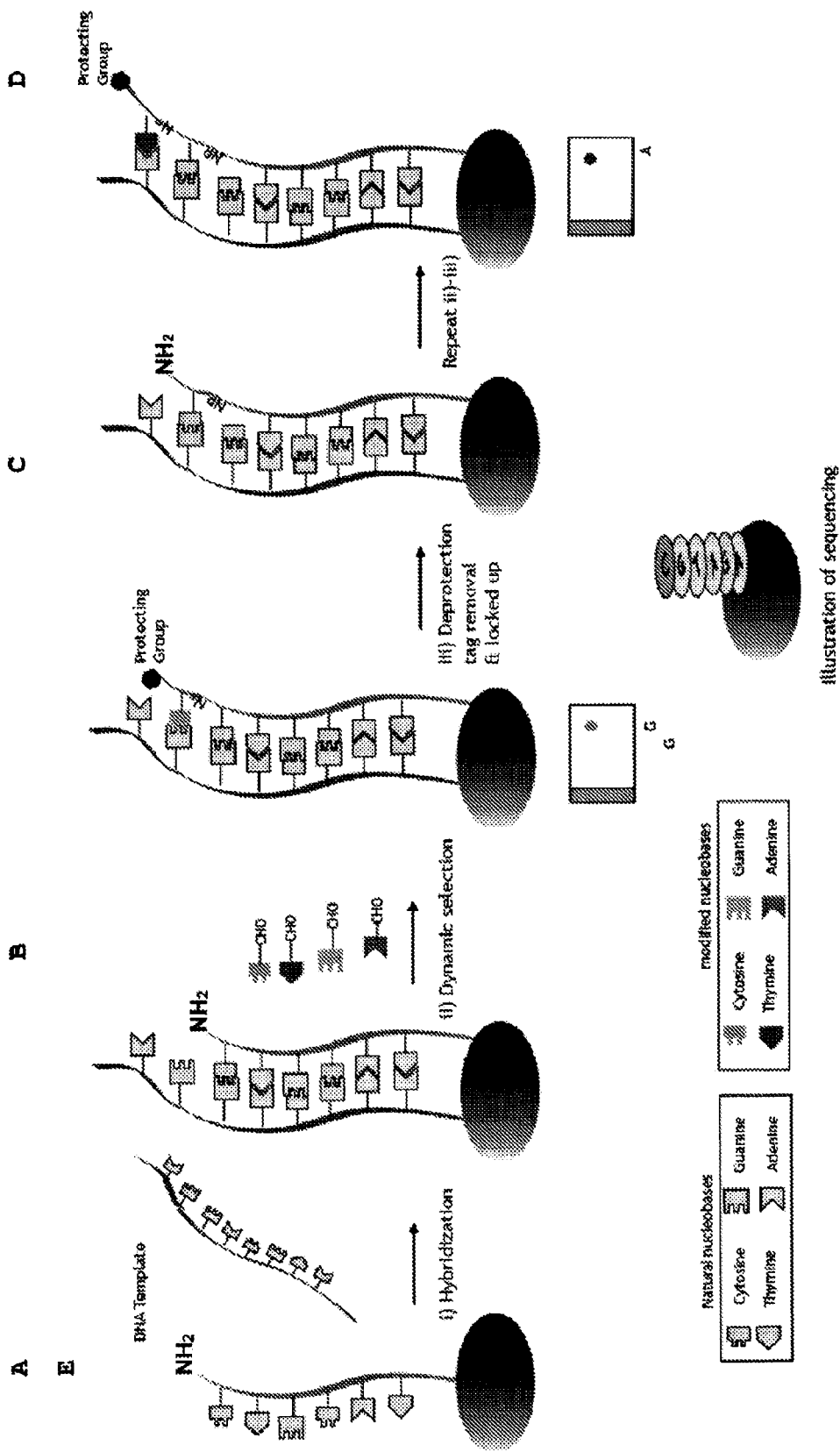

FIG. 6: Illustration of dynamic-based DNA sequencing. (a) PNA oligomers, which may be attached to surfaces or in solution, containing a free amino group at the N-terminal position (b) DNA templates hybridise to their corresponding "PNA primers" (c) addition of the four N-protected aldehyde PNA monomers (d) dynamic attachment of the corresponding nucleobase (e) removal of both protecting groups and tags "fixing" the growing strand by may be a reduction process and repeat.

Figure 7:
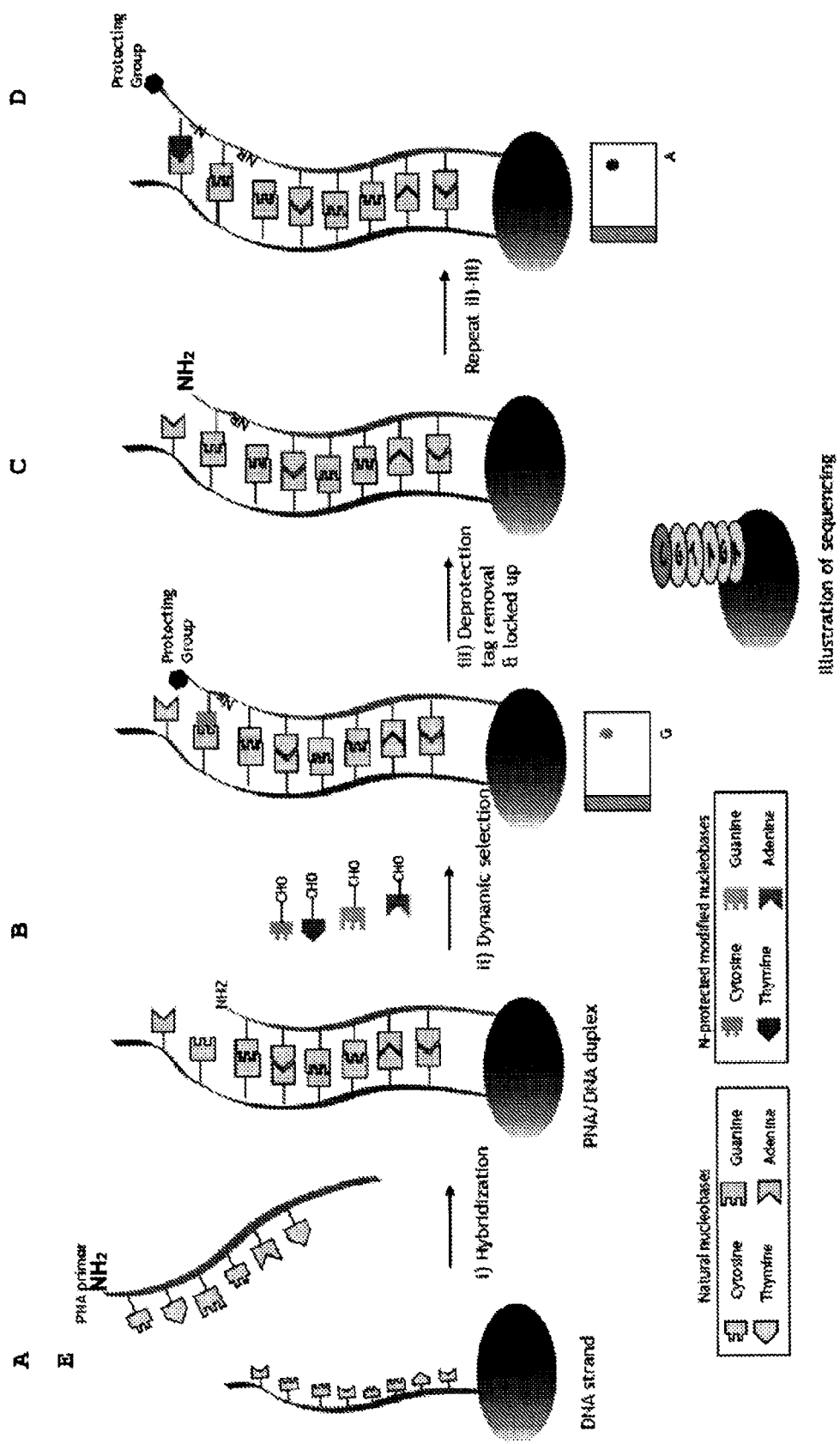

FIG. 7: Illustration of dynamic-based DNA sequencing. (a) DNA oligomers, which may be attached to surfaces or in solution (b) "PNA primers" having a free amine group at their N-terminal position hybridise to their corresponding DNA template (c) addition of the four N-protected aldehyde PNA monomers (d) dynamic attachment of the corresponding nucleobase (e) removal of both protecting groups and tags and "fixing" the growing strand by may be a reduction process and repeat.

Figure 8:
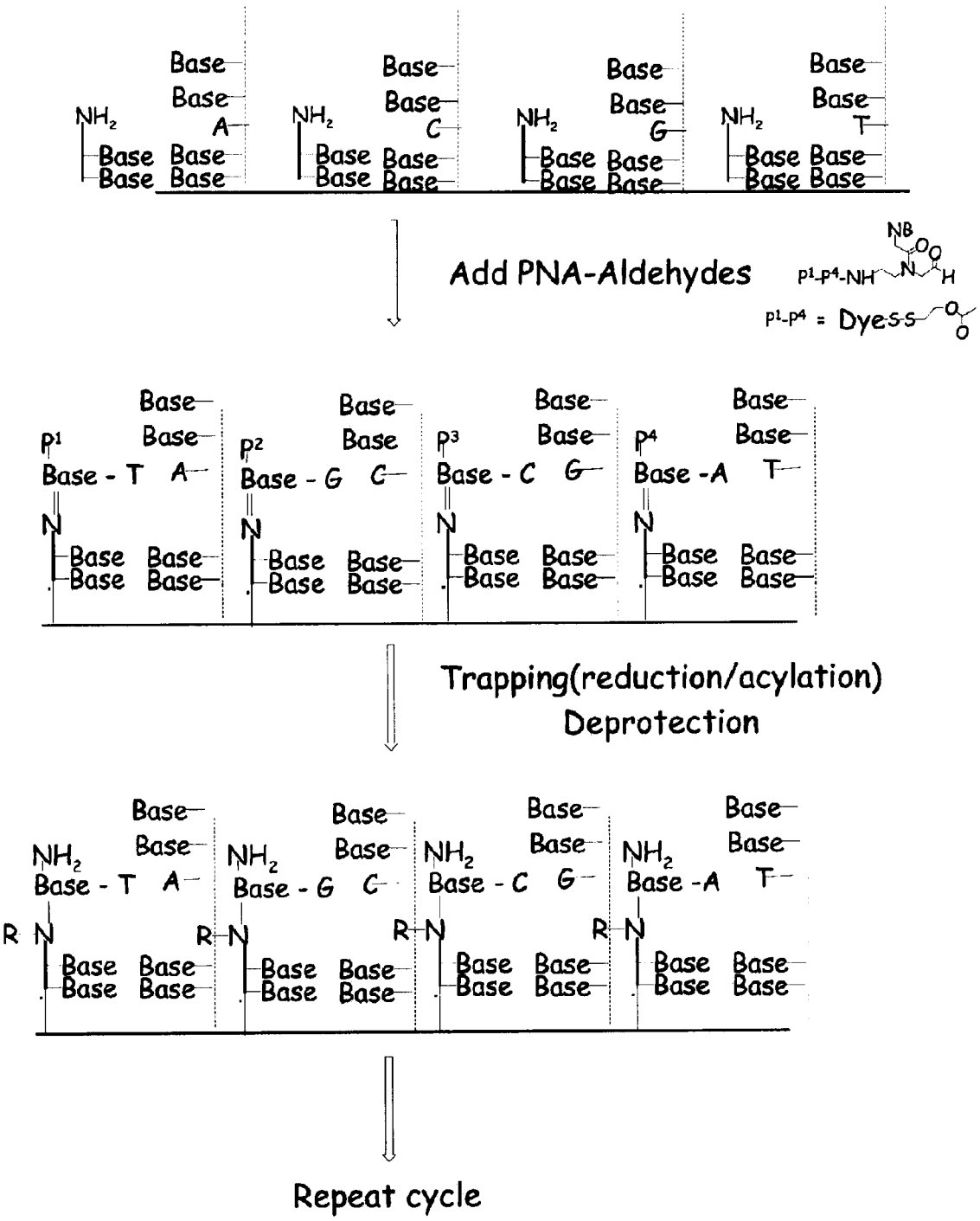

FIG. 8: Dynamic-based DNA sequencing of FIGS. 6 and 7.

Figure 9:
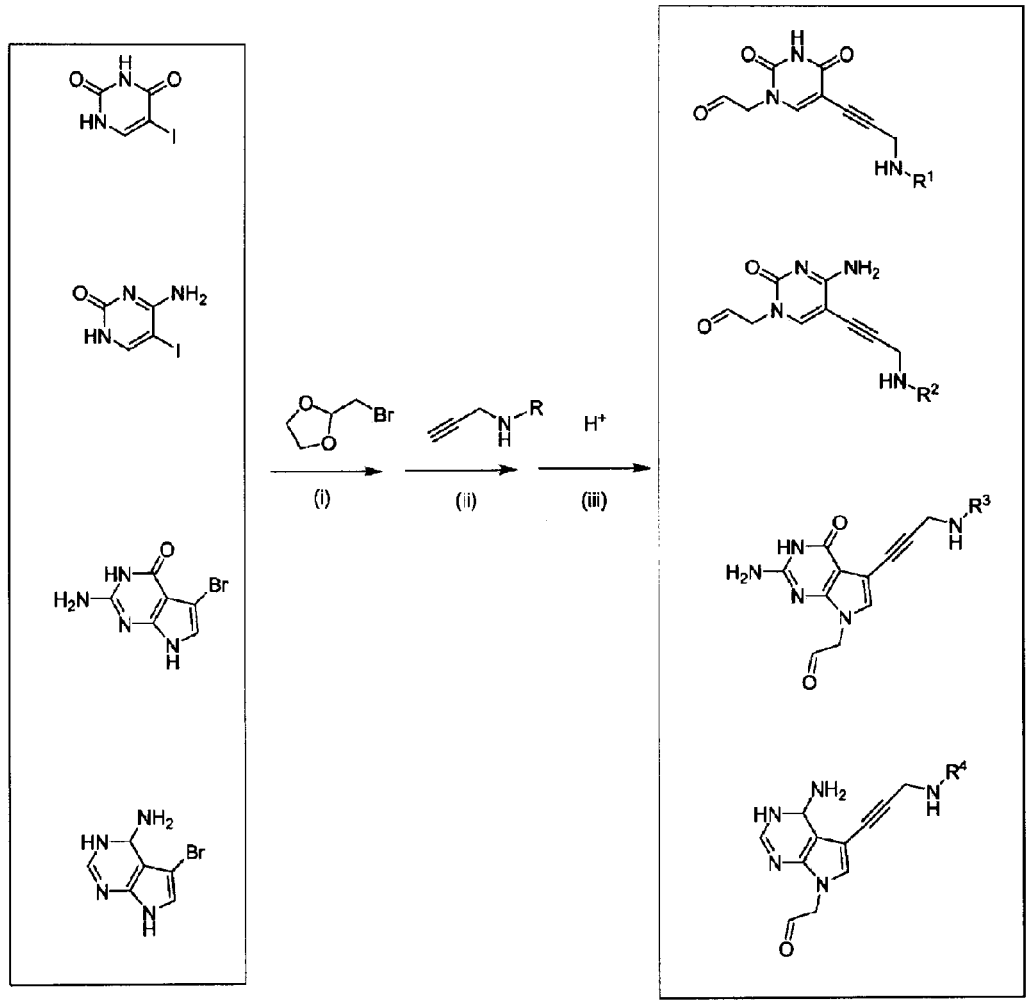

FIG. 9: Synthesis of aldehyde bases (i) N-alkylation of nucleobase using a bromoalkyl acetal (ii) labelling of the nucleobases via Sonogashira reaction (iii) deprotetion of the acetal protecting group.

Figure 10:
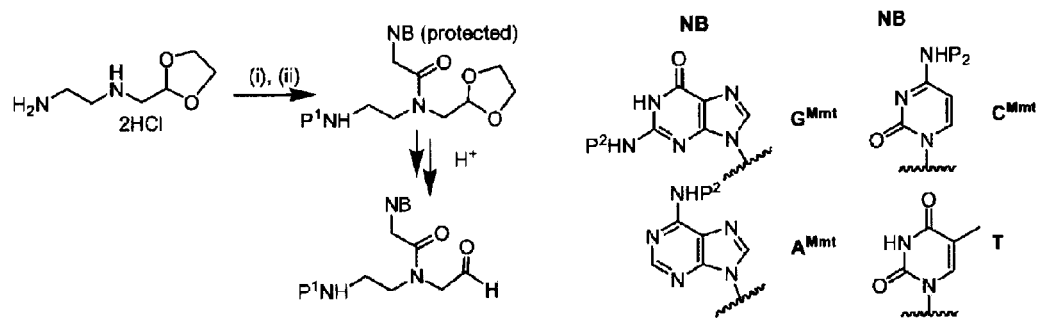

FIG. 10: Synthesis of protected/tagged PNA-aldehydes: (i) Protection of primary (ii) $C^{Mmt}CH_2COOH$, $A^{Mmt}CH_2COOH$ or $G^{Mmt}CH_2COOH$ or $T-CH_2COOH$, DCC, HOBt; NB=Nucleobases.

Figure 11:
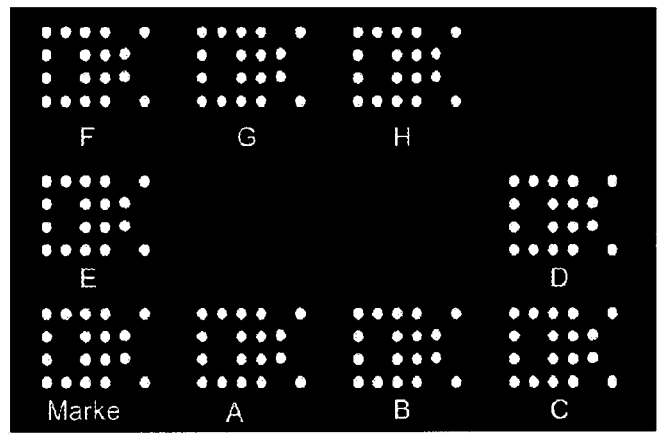

FIG. 11: Schematic representation of the pattern followed to print 8 DNA oligomers (Table 1) and a fluorescently-labelled marker.

Figure 12:
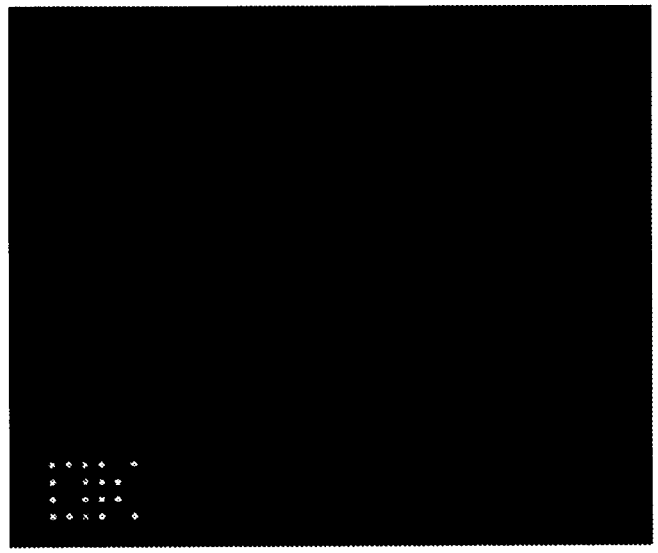
Figure 13:
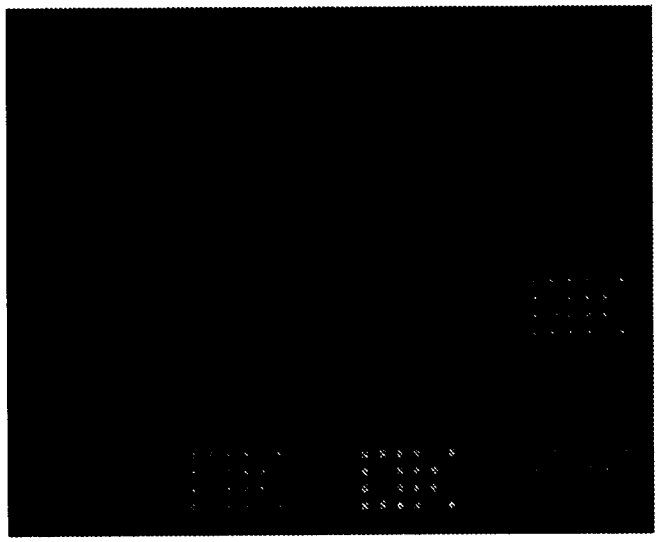

FIG. 12: FITC channel image of slide containing 8 DNA oligomers (Table 1) plus a fluorescent DNA marker hybridized with PNA 13 containing a blank position. Just the fluorescent DNA marker is detected;

FIG. 13: Cy5 channel image of slide containing 8 DNA oligomers (Table 1) plus a fluorescent DNA marker hybridized with PNA 13 containing a blank position, only PNA-DNA antiparallel orientated duplexes were able to hybridise.

Figure 14A:
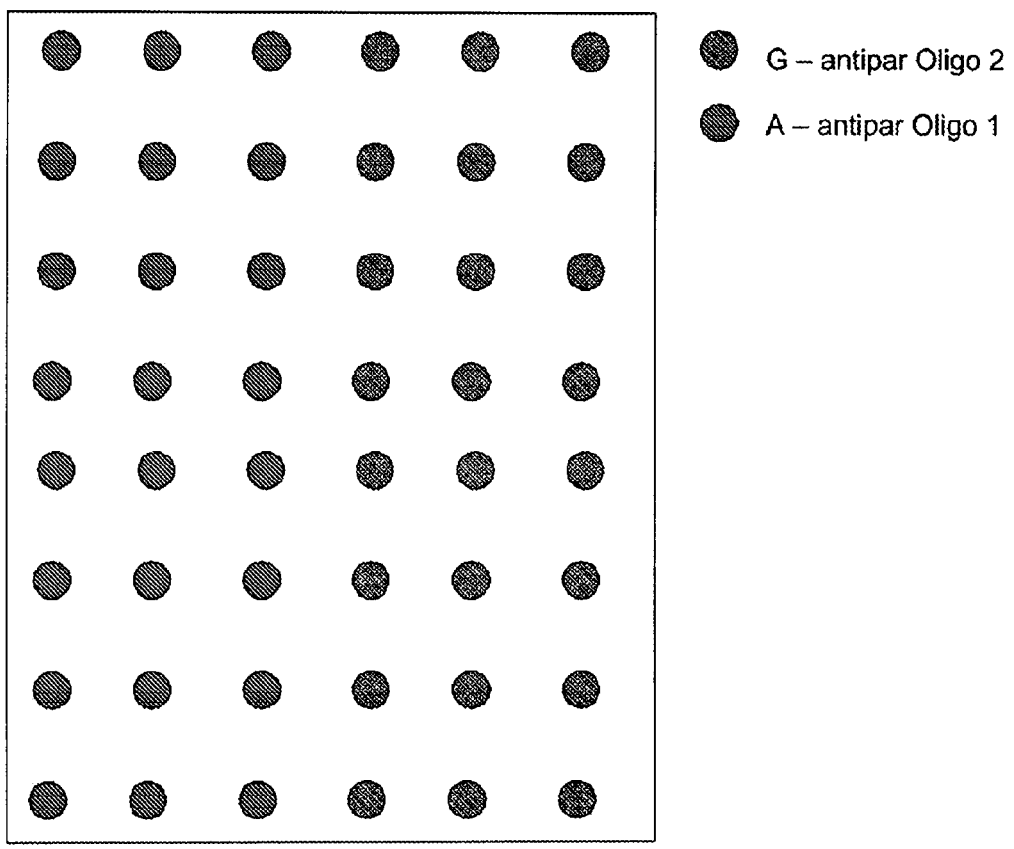
Figure 14B:
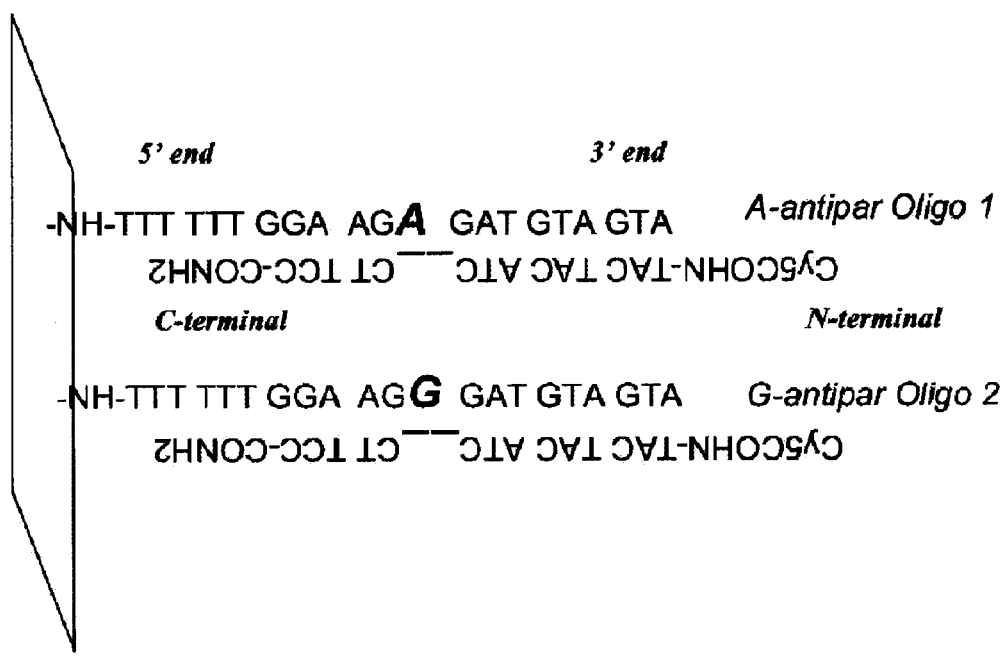

FIG. 14: (A) Shows the pattern of amino modified oligonucleotides (Table 2) printed onto aldehyde slides using a Microdrop robot equipped with a piezo electric pipette (3×8 pattern). (B) Schematic representation of antiparallel duplexes formed by PNA 13 and DNA oligonucleotides found in Table 2. (C) Fluorescent image (Cy5 channel) showing PNA 13 hybridised with oligo 1 and 2 (Table 2). (D) FITC channel image showing the dynamic incorporation of fluorescein-labelled cytosine aldehyde 10 following incubation of arrays containing DNA-PNA 13 duplexes with aldehydes 9 and 10. Fluorescein signal was detected only where G-antipar oligo 2 (Table 2, FIGS. 14A and 14B) was printed. (E) Further FITC channel image showing the results of an in situ approach and the dynamic incorporation of fluorescein-labelled cytosine aldehyde. Fluorescein signal was detected only where G-antipar oligo 2 (Table 2, FIGS. 14A and 14B) was printed FIG. 15: (A) Synthesis of aldehyde dimers for dynamic sequencing where the second nucleobase is defined by a dye. (B) A PNA dimer in which the first nucloebase is identified by a dye.

Figure 16A:
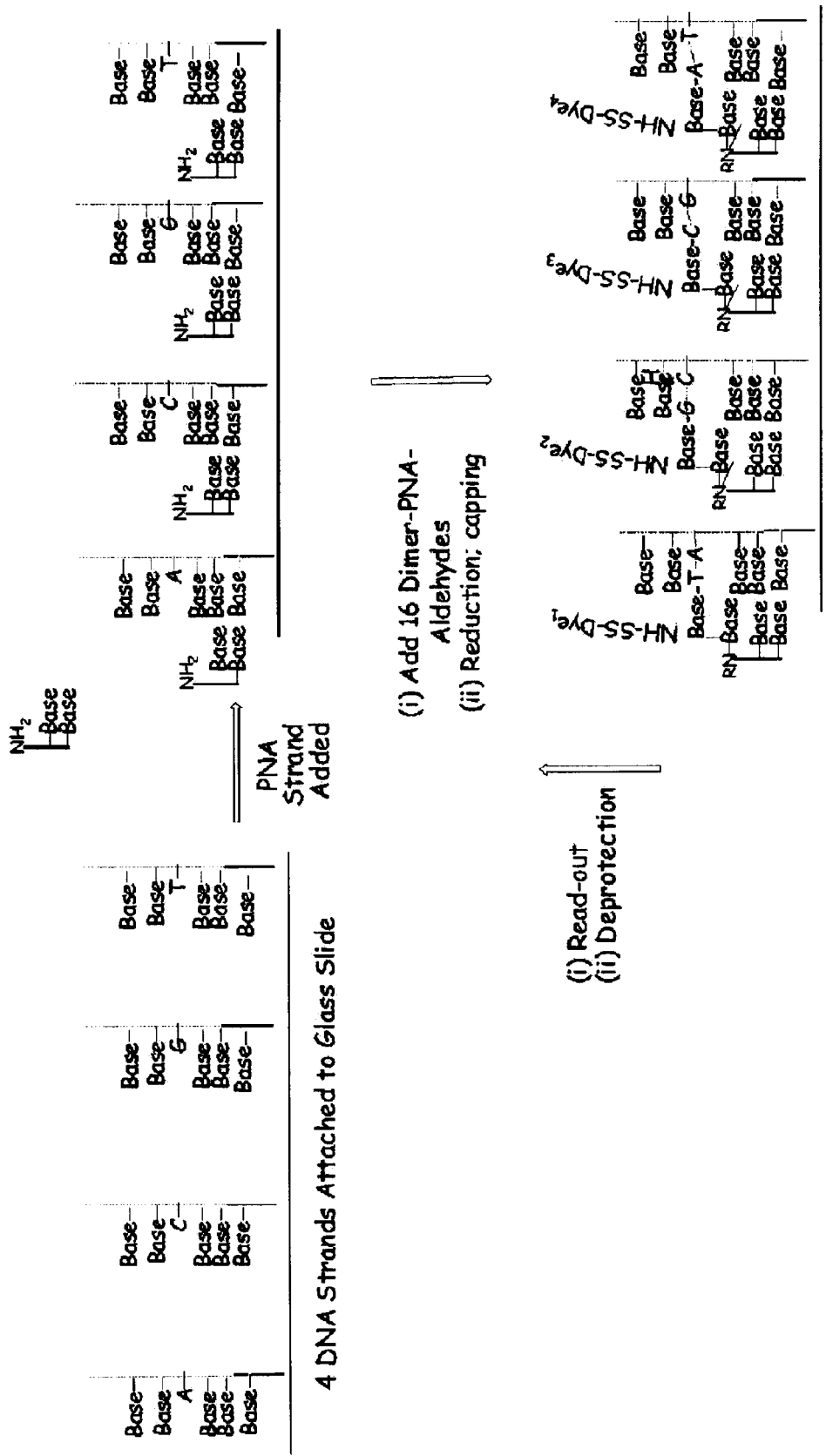
Figure 16B:
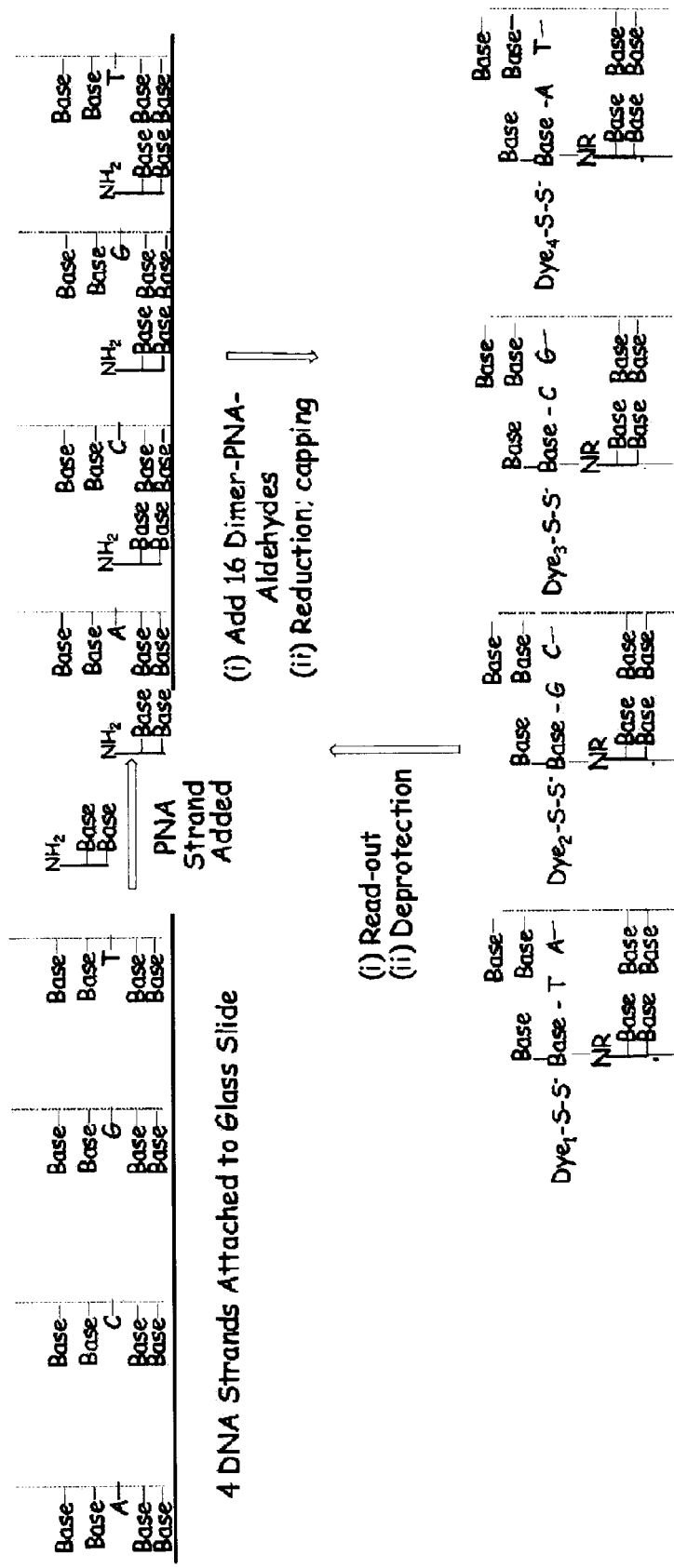

FIG. 16: (A) Nucleotide characterisation method using PNA dimers in which the second nucleobase of the dimer is labelled with a detectable tag. (B) Alternative method of nucleotide characterisation utilising PNA dimers in which the first nucleobase is labelled with a detectable tag.

Figure 17:
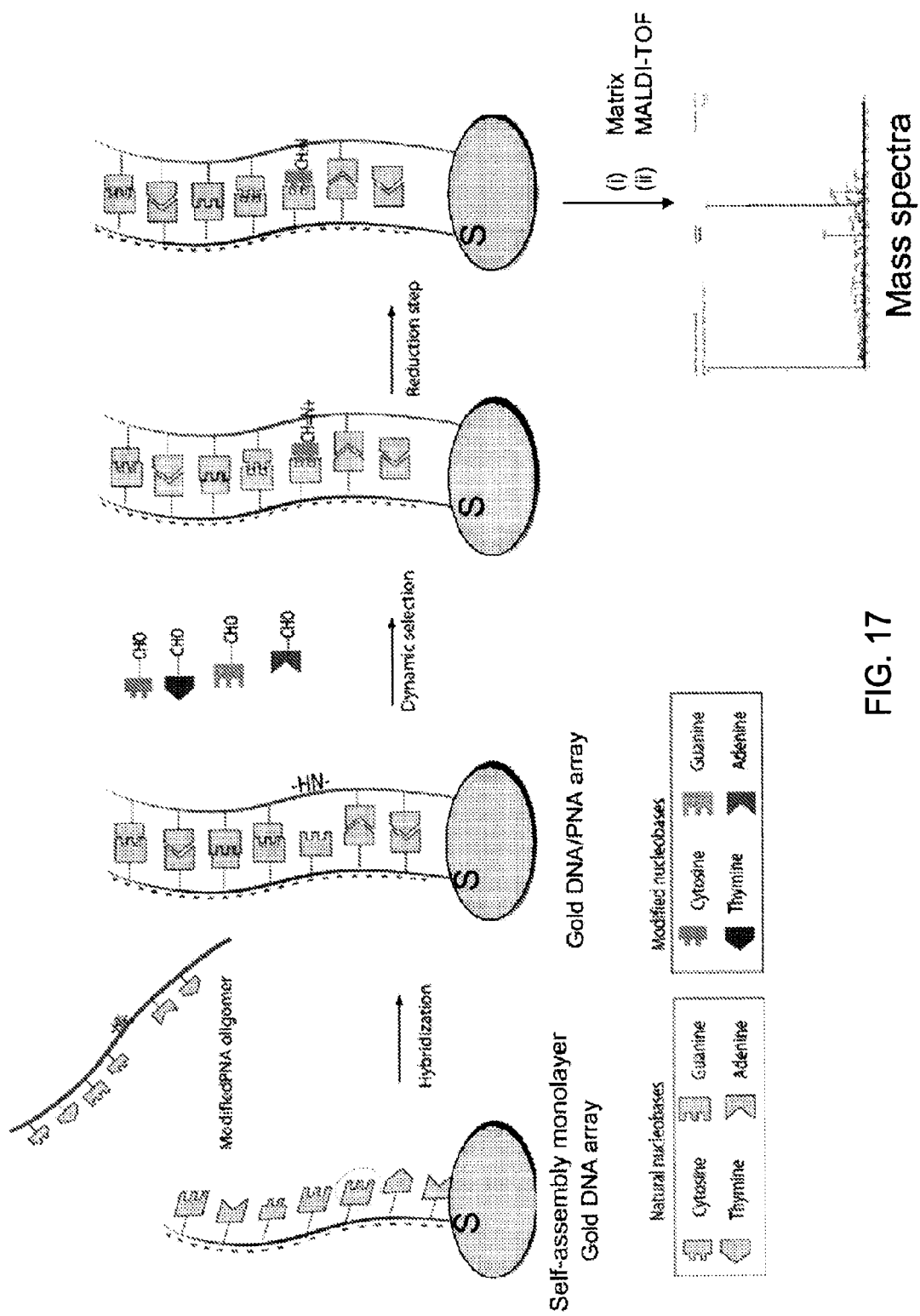

FIG. 17: schematic diagram showing a method for mass-spectrometry based SNP analysis.

Figure 18:
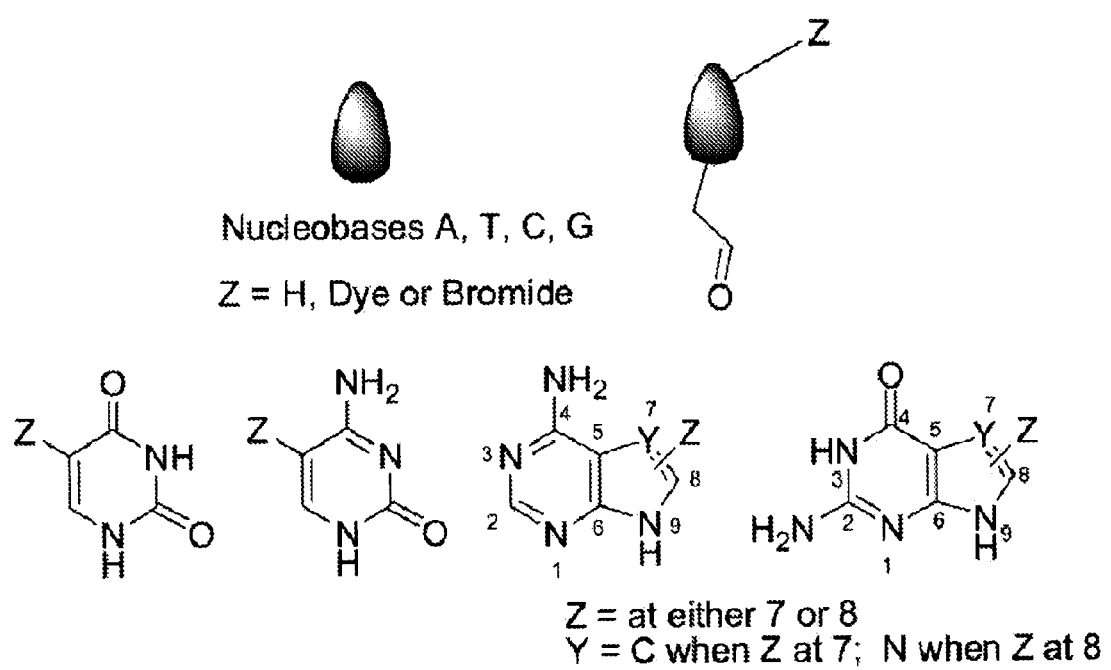

FIG. 18: Shows the general structure of the modified nucleobases for use in mass-spectrometry based SNP analysis.

Figure 19:
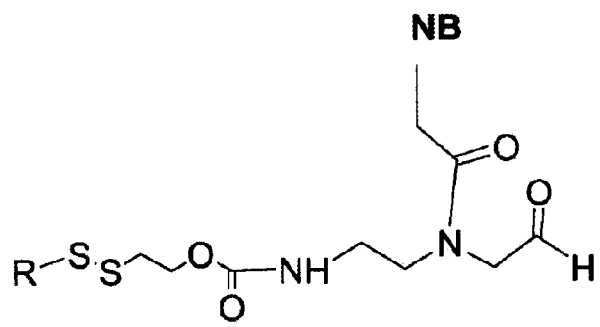
Figure 19:
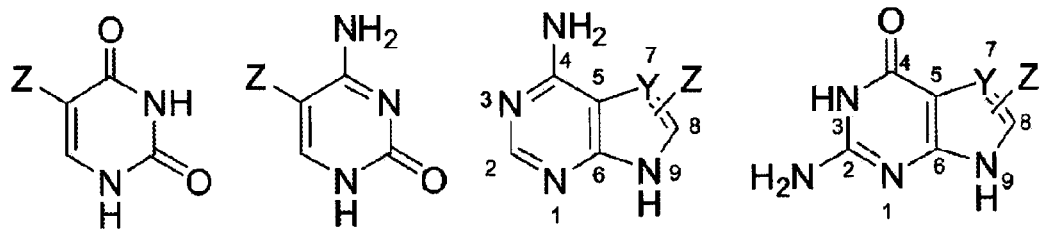

FIG. 19: Shows the general structures of modified nucleobases which may be useful in mass-spectrometry based nucleic acid sequencing methods.

METHODS

Synthesis of the Labelled Bases, Building Blocks and Primers (i). PNA-aldehyde monomers and aldehyde bases. These were prepared as shown in FIGS. 9 and 10. This method is applicable to many protecting groups groups and this includes the Dde group, the Fmoc group, thiol cleaved protecting group (Ardec (aryldithioethyloxycarbonyl) light cleavable protecting groups (nitroveratyl based) as well as fluorophores.

The above detailed methods may be adapted to give fluorescent labelled materials via classical Sonogashira coupling of the bromo and iodo-pyrimidine and purine derivatives to propargylamines followed by fluorescent labelling with the various fluorophores (see Scheme 3). This approach may also be applied to the synthesis of the fluorescently labelled "aldehyde bases" (FIG. 6). The fluorophore choice will be dictated by the need to allow individual detection of bases.

Synthesis of protected and tagged PNA-aldehydes

PNA-aldehydes 2 were prepared from PNA carboxylic acids, PNA esters or PNA alcohols following standard chemistries (Scheme 1). 1 was prepared according to a published methods (L. Bialy et al. *Tetrahedron* 2005, 61, 8295-8305).

Scheme 1. Target synthesis.

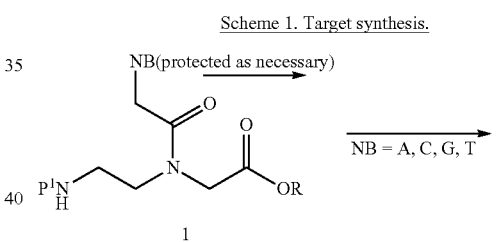

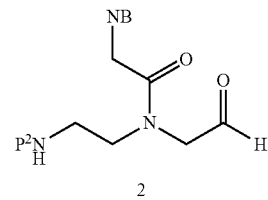

As an example 3 was converted into a Weinreb amide 4 (Scheme 2), then reduced to afford the target aldehyde 2. To prevent over-reduction of 4, the milder reducing agent lithium tri-tert-butoxyaluminium hydride (LiAlH(O-t-Bu)$_3$) was employed in place of LiAlH$_4$ (M. Paris et al. *Tetrahedron Lett.* 1998, 39, 1341-1344).

Scheme 2. Synthesis of target aldehyde via reduction of a Weinreb amide: (a) MeONHMe•HCl, EDC•HCl, HOBt•H$_2$O, Et$_3$N, DMF, room temperature; (b) LiAlH(O-t-Bu)$_3$, THF, room temperature. 65% yield (HPLC).

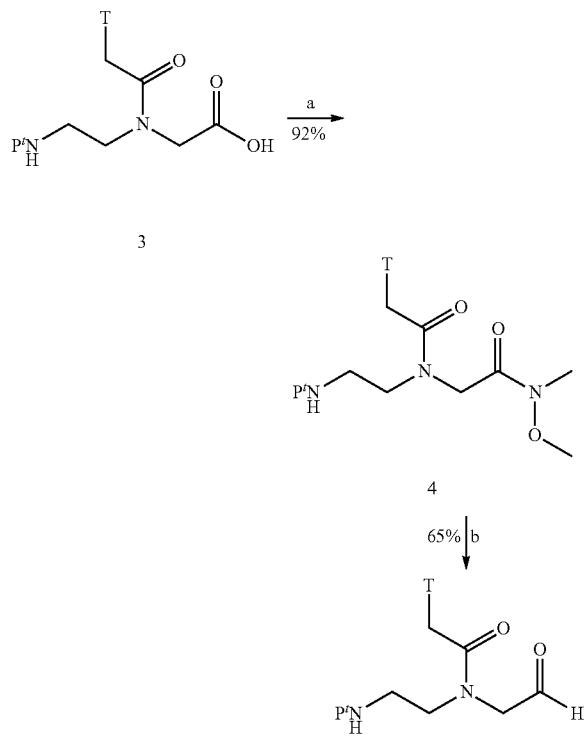

T = 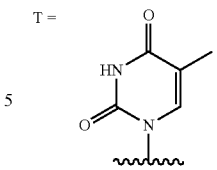

Aldehydes were purified using a catch-and-release strategy on a threonyl resin (D. R. Liu et al. *J. Am. Chem. Soc.* 2003, 125, 13924-13925).

(a) Preparation of resin: Aminomethyl NovaGel HL was swollen with DMF over approximately 10 min. Meanwhile, DIPEA was added to a solution of Fmoc-Thr(t-Bu)-OH and TBTU in DMF and the reaction mixture was shaken for 5 min. The swollen resin was then filtered and the solution of activated protected threonine was added. The resulting suspension was shaken at room temperature for 2 h. The resin was then filtered from the reaction mixture and washed with DMF (5×), THF (5×) and DCM (5×), then dried in vacuo at 40° C. overnight. The resin was then swollen in DMF for approximately 10 min and filtered, then shaken with 20% v/v piperidine in DMF ×2. The resin was then shaken with 80% v/v TFA (trifluoroacetic acid) in DCM, filtered, washed with DCM (1×) and again shaken with 80% v/v TFA in DCM. The resin was filtered, washed with DCM (5×) and dried in vacua at 40° C.

(b) Purification of Aldehyde by Catch and Release:

Capture: To the deprotected threonyl scavenging resin was added a solution of crude aldehyde. The mixture was shaken at room temperature for 1 h, then the resin was filtered and washed. Release: The resin was shaken and washed with a mixture of AcOH/H$_2$O/DCM/MeOH (10/5/5/80, 2 mL×5) for 20 min and the washings concentrated in vacuo to give the aldehyde.

Scheme 3. Condensation of the impure aldehyde with a threonine modified resin yields a supported oxazolidine. After washing, cleavage affords the pure aldehyde.

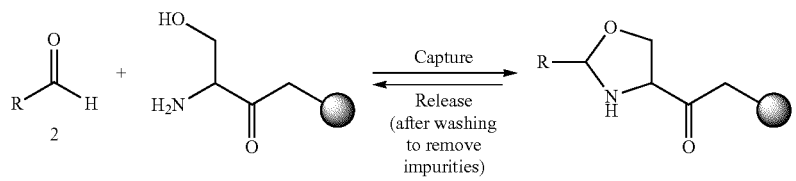

R = 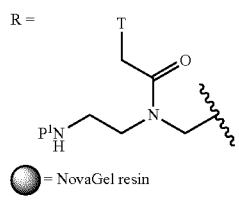

● = NovaGel resin

1. An alternative route to aldehyde 2 is via the S-benzyl thioester 5 as shown in Scheme 4 (P. T. Ho, et al. *J. Org. Chem.* 1993, 58, 2313-2316).

Scheme 4.

Synthesis of target aldehydes via the S-benzyl thioester:

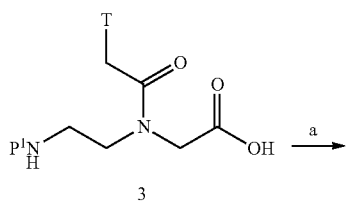

(a) benzyl mercaptan, DMAP, DCC, DMF room temperature, (b) triethylsilane, Pd/C, THF, room temperature, 20 h, 95% yield (HPLC).

Alternative routes include the reduction of the methyl ester to the corresponding primary alcohol and subsequent oxidation or direct synthesis of the PNA alcohol and oxidation.

Synthesis of Tagged Nucleobases-Aldehydes for SNP Analysis (Method 1)

Nucleobases-aldehydes 6 were prepared from commercial available halo-nucleobases by alkylation with 2-(bromomethyl)-1,3-dioxolane (Scheme 5) under microwave irradiation followed by Sonogashira reaction with Tfa protected propargylamine, deprotection of the Tfa protecting group and coupling with a carboxylic acid derivatised dye.

Scheme 5. General strategy for synthesising nucleobase-aldehyde.

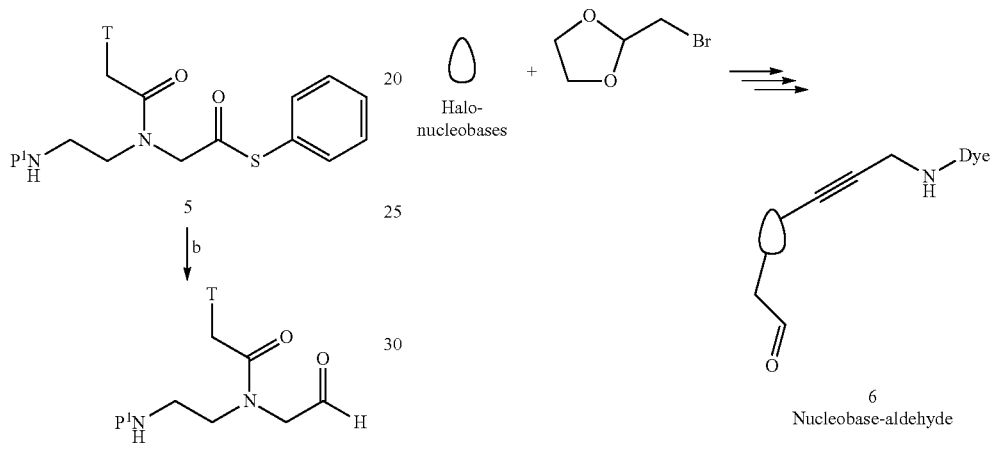

As an example thymine and cytosine derivative were synthesised as described in Scheme 6 and 7.

Scheme 6. Synthesis of rhodamine labelled cytosine-aldehyde 7

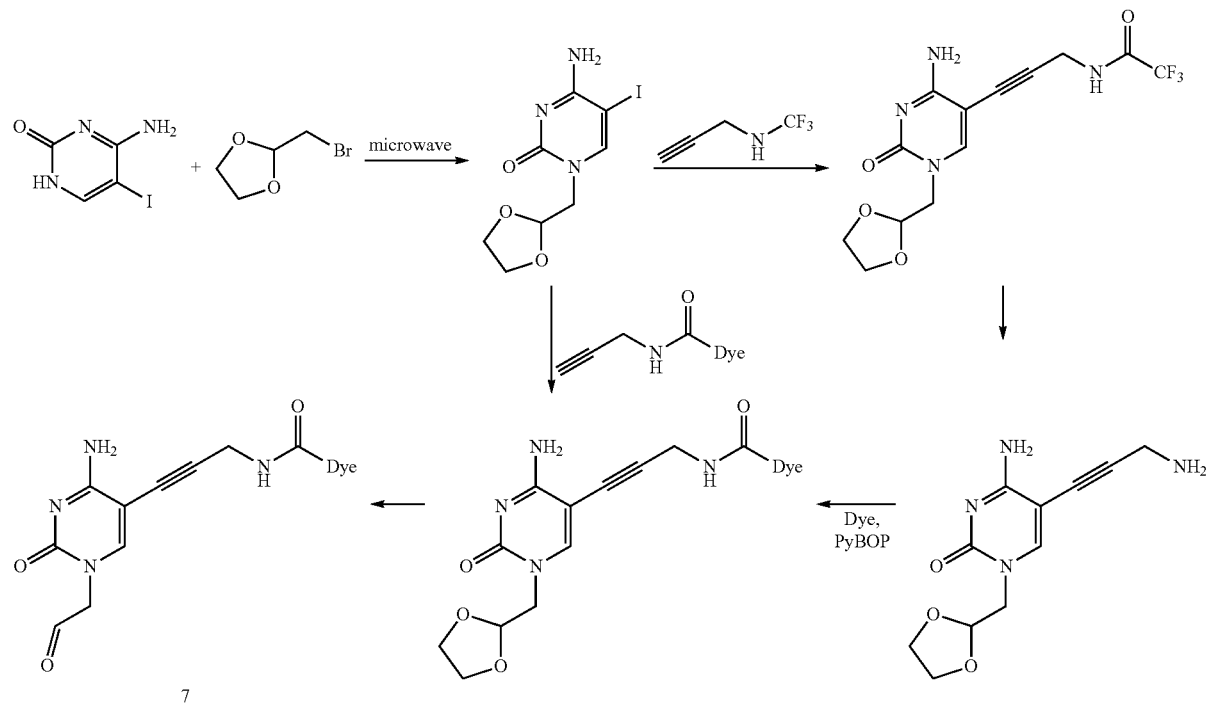

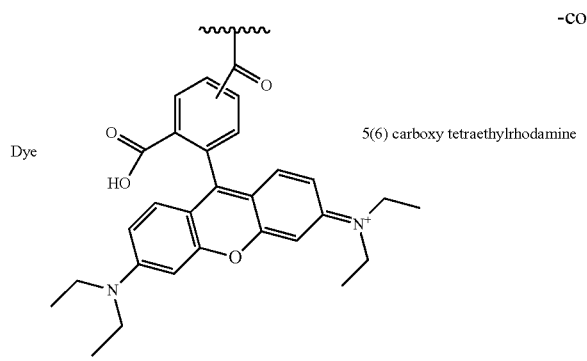

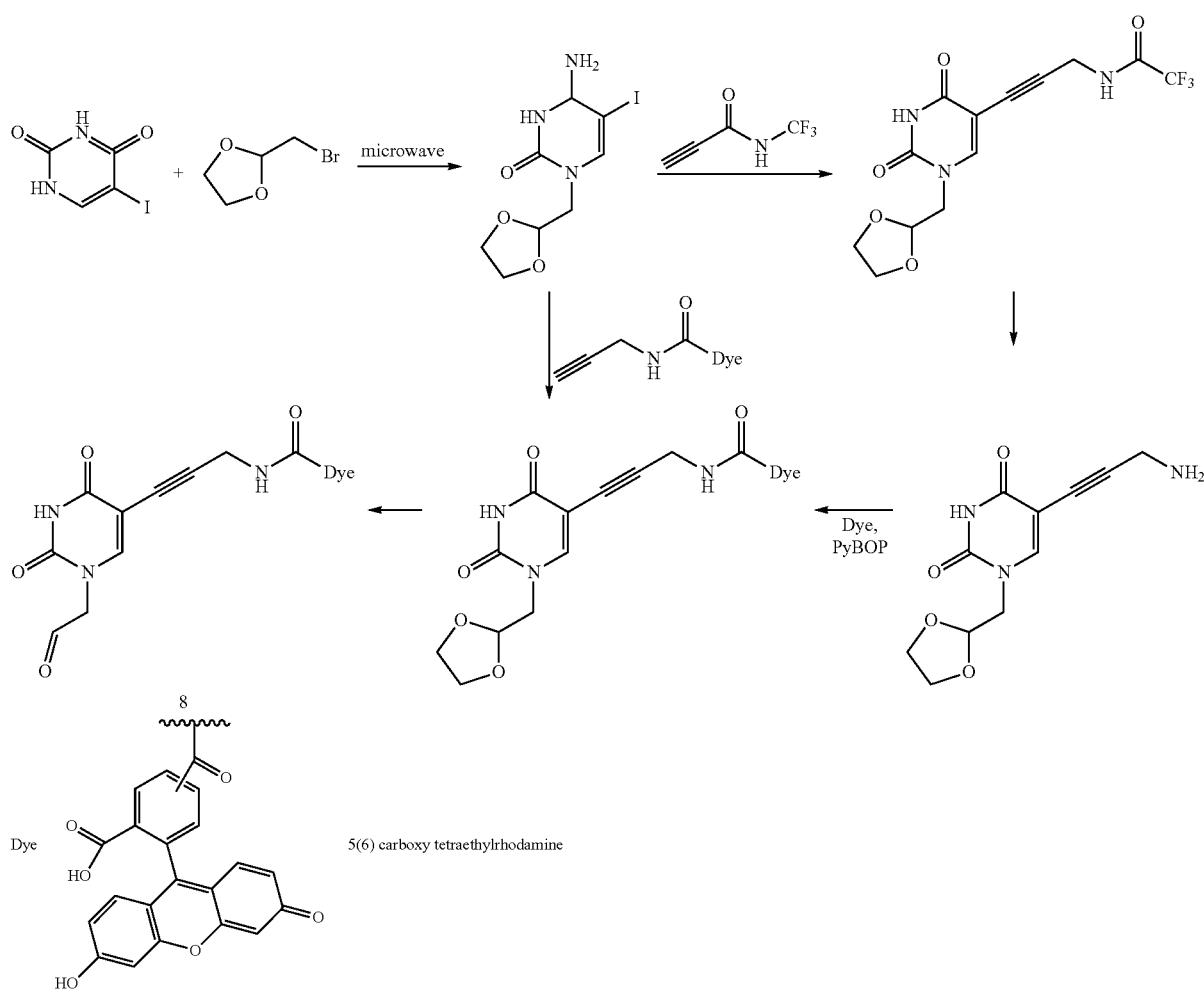

Alkylation of Nucleobases with Acetals

This process was optimised using microwave irradiation at 100° C. for 30 min in THF. The use of 1.2 equiv. of 2-(bromomethyl)-1,3-dioxolane with $NEt_3$ gave rise to the monoalkylated product in a 4:1 ratio.

The labelling of the nucleobases were achieved via Sonogashira cross coupling reaction using aminomethylacetylene.

(a) Sonogashira reaction with Tfa protected aminomethylacetylene before deprotecing the Tfa group with ammonia. PyBOP as coupling agent.

(b) The second explored pathway was to carry out the Sonogashira reaction with the acetylene group already bearing the dye. That reaction was done by reacting aminomethyl acetylene with supported activated dyes using a hydroxynitrobenzoic resin (Scheme 8).

Scheme 8. Synthesis of labelled acetylene using supported activated dyes.

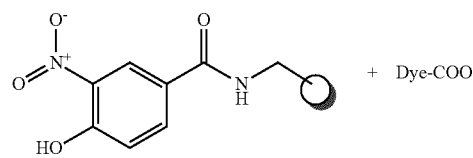

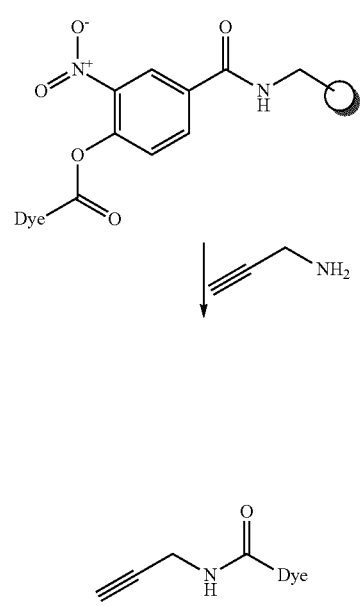

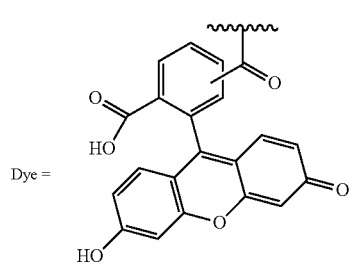

Dye =

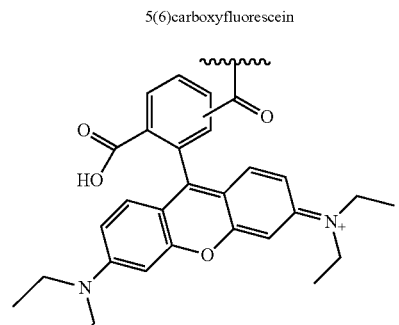

5(6)carboxyfluorescein

5(6) carboxytetraethylrhodamine

Finally, acetals were deprotected using 2N HCl in $H_2O$ to give products 7 and 8.

Synthesis of Fluorescently-Labelled Aldehyde Bases for "Clamp" SNP Analysis

The alkylation of the nucleobases was achieved using a modified procedure described by L. Christensen et al., *Nucl. Acids Res.*, 1998, 26, 2735-2739. One equivalent of halogenated nucleobase was dissovled in DMF with NaH (1.2 equivalent) and then stirred for 30 min at room temperature. Then, 1.12 equivalent of bromoacetaldehyde diethylacetal was added and the solution stirred under microwave irradiation for 30 min at 130° C.

Alkylated halobases were subjected to Sonoghasira crosscoupling following a procedure described in N. K. Garg et al. *Chem. Commun.*, 2005, 4551-4553 and using Tfa protected aminomethylacetylene. Deprotecing the Tfa group with ammonia in MeOH, gave rise to a free primary amine which was used to couple dyes containing carboxylic groups. The amide coupling was achieved using HOBt/EDCI HCl coupling agents.

Acetal deprotection was achieved by treatment with 75% TFA/12.5% $H_2O$/12.5% $CH_3CN$ during 24 hours at room temperature. Alternatively, by heating at 60° C. under microwave irradiation for 2 hours. Acetals were purified by RP-HPLC. RP-HPLC was performed on a HP1100 system equipped with a Phenomenex Prodigy C18 reverse-phase column (250 mm×10 mm×5 mm) with a flow rate of 2.5 mL/min and eluting with (A) 0.1% TFA in $H_2O$ and (B) 0.042% TFA in acetonitrile, with an initial isocratic period of 4 min at 0% (B) followed by a gradient of 0-50%. (B) over 25 min and 50-100% (B) over 10 min, holding at 100% (B) for 5 min. ESI-/MS analyses were carried out on an Agilent Technologies LC/MSD Series 1100 quadrupole mass spectrometer (QMS) in a electrospray ionization (ESI) mode. Final aldehydes were identified by NMR and LC-MS (ESI).

As examples, rhodamine-labelled thymine aldehyde (Scheme 9) and fluorescein-labelled cytosine aldehyde (Scheme 10) were produced as described above. Nucleobases modified in this way may be used in any of the methods described herein and in particular, in methods for SNP characterisations and/or analysis.

Scheme 9-Synthesis of rhodamine-labelled thymine 9 aldehyde for SNP analysis using the "clamp" approach.
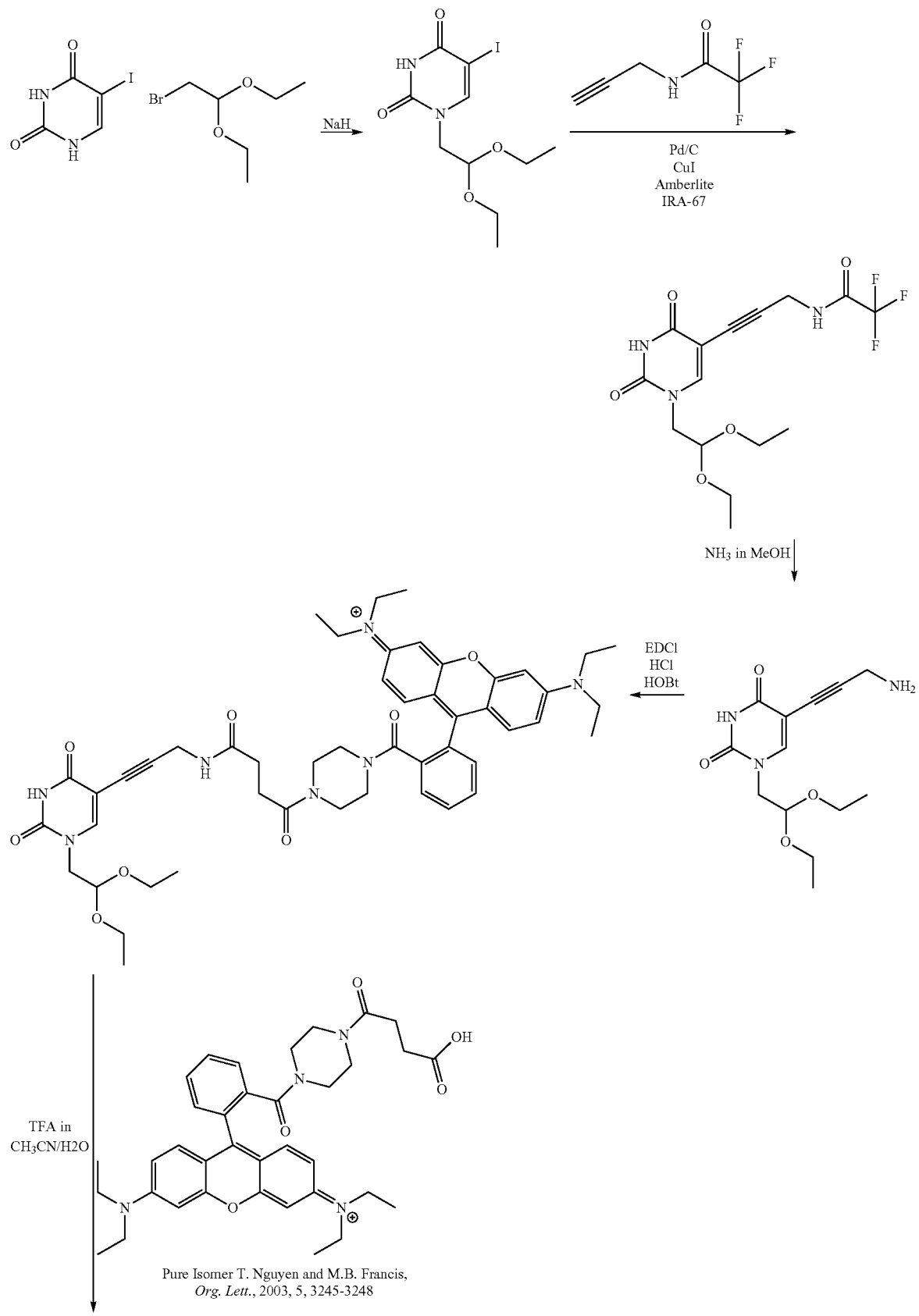

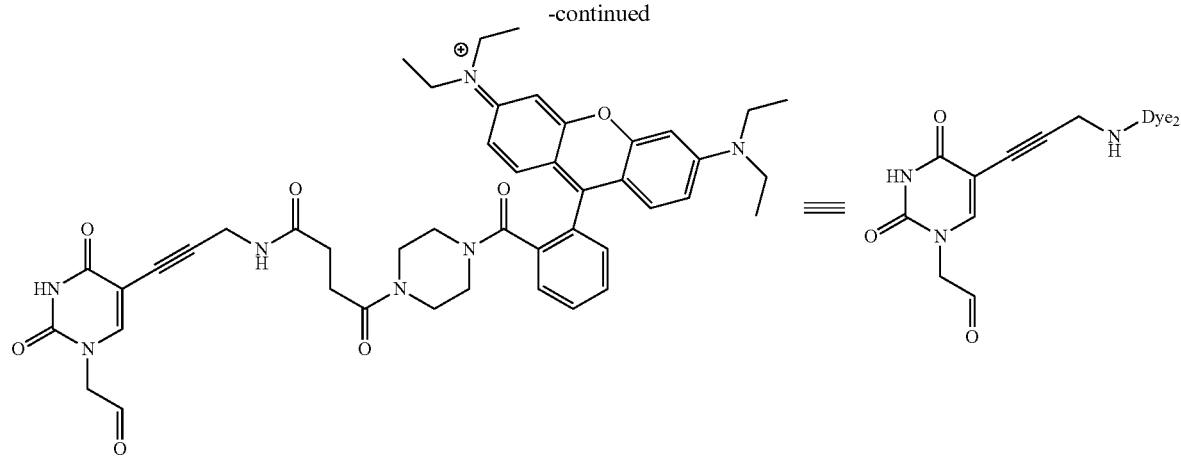
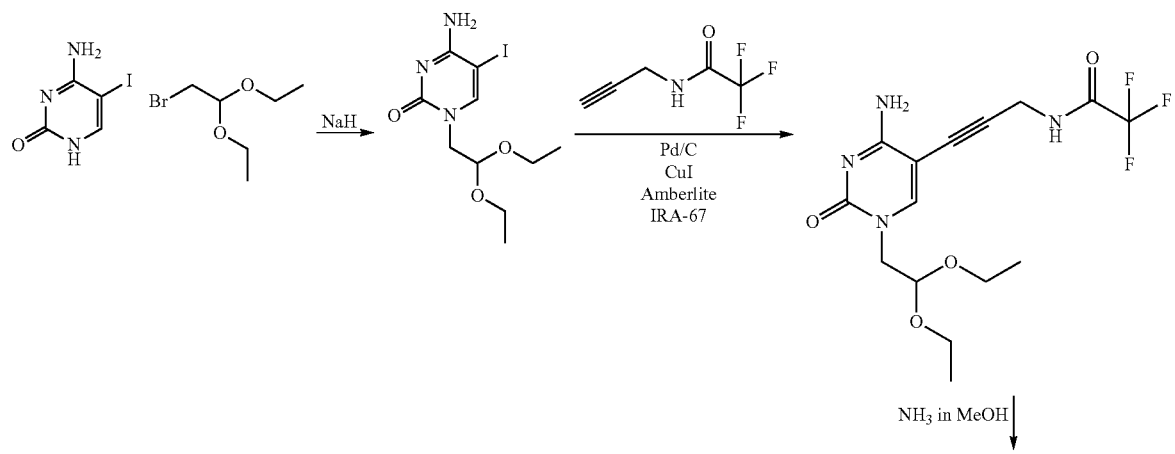
Scheme 10-Synthesis of fluorescein-labelled cytosine aldehyde 10 for SNP analysis using the "clamp" approach.
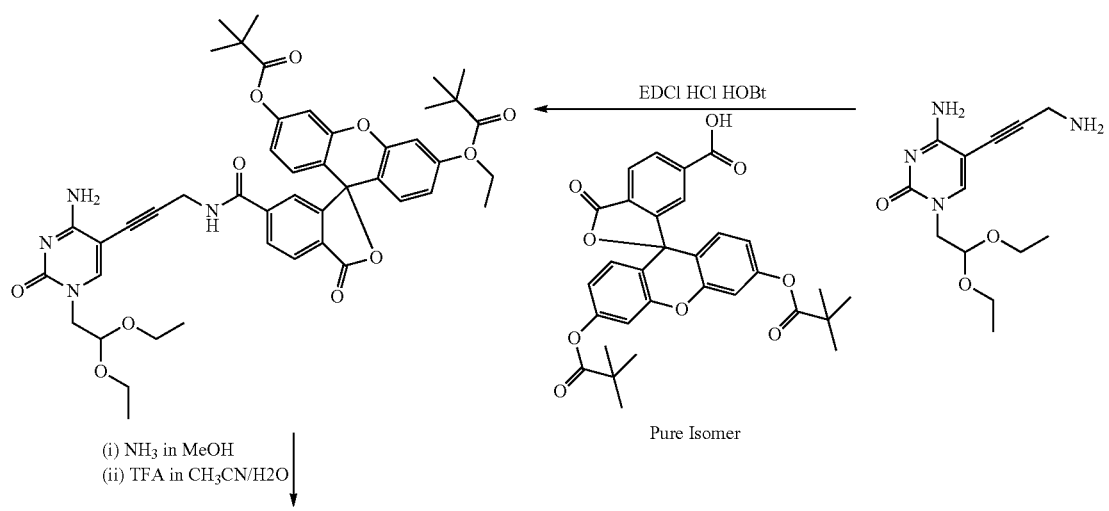

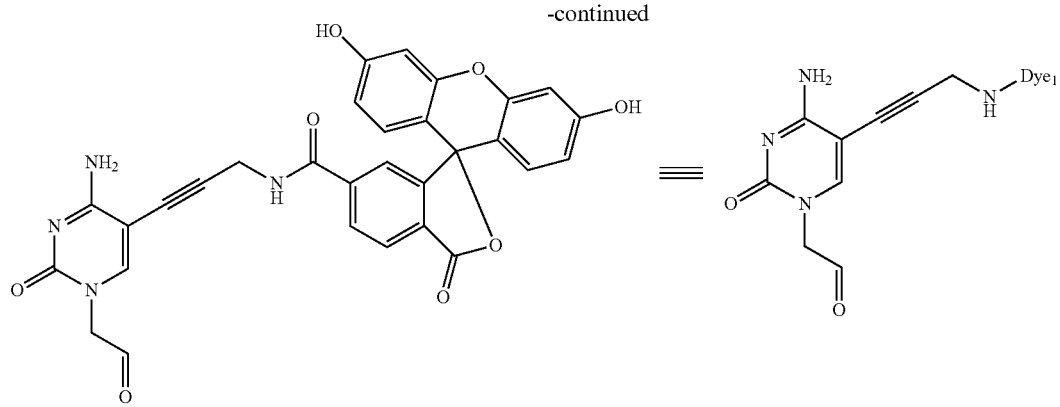

10

One of skill in this field will appreciate that adenine and guanine derivatives using BODIPY dyes will prepare in a similar manner. In such cases the halonucleobases are the following:

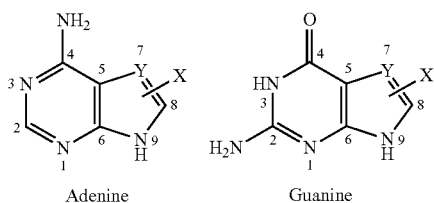

Adenine    Guanine

X = Br at either 7 or 8
Y = C when X at 7; N when X at 8

Synthesis of N-2(Dde-amino)ethyl-N-boc-glycine 11

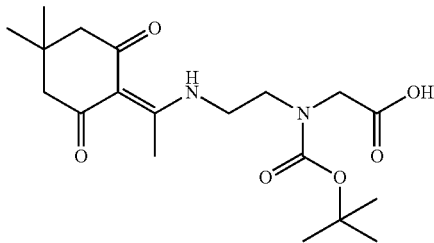 [SMILES: CC(NCCN(CC(=O)O)C(=O)OC(C)(C)C)=C1C(=O)CC(C)(C)CC1=O]

To a solution of methyl N-2(Dde-amino)ethyl-glycine ester (1_mmol) (L. Bialy et al., *Tetrahedron*, 2005, 61, 8295-8305) in dry THF (10 mL, 0.1 M) was added Boc$_2$O (1.1 mmol) and triethylamine (1.1 mmol) and the reaction was stirred for 5 hours being monitored by TLC. After removal of the solvent the crude was dissolved in DCM and washed with NaHCO$_3$, KHSO$_4$ and brine. The organic phase was dried over NaSO$_{4\ anh}$. and concentrated to give rise to a yellow solid. Without any further purification the crude was dissolved in MeOH and a 2 M solution of Cs$_2$CO$_3$ in water was added. After 1.5 h the reaction was acidified to pH 3 with KHSO$_4$. The acid precipitated, filtered off and dried to give rise acid 11 as a white solid.

Synthesis of PNA Oligomers 12 and 13

PNA oligomer 12 (H$_2$N-TACTACATC_CTTCC-CONH$_2$) and 13 (Cy5COHN-TACTACATC_CTTCC-CONH$_2$)_=boc-deprotected blank monomer 9 were synthesised using Dde protected monomers (Bradley et al., *Tetrahedron*, 2005, 61, 8295-8305) on solid phase (J. J. Diaz-Mochon et al., *Org. Lett.* 2004, 6, 1127-1129). In order to insert the blank monomer N-2(Dde-amino)ethyl-N-boc-glycine 11 was used.

HPLC and MALDI-TOF

PNA 12 (MALDI-TOF; calculated mass: 3780, found mass: 3781 (M+1).

PNA 13 (MALDI-TOF; calculated mass: 4244, found mass: 4246 (M+1).

Array Based Screening.

8-amino modified oligonucleotides (Table 1) were contact printed onto Code-link (Amersahm) slides for SNP analysis. These oligos were designed to have either a parallel orientation (PNA C-terminal facing DNA 3'-end) when hybridised with PNA 13 or antiparallel (PNA N-terminal facing DNA 3'-end).

TABLE 1

DNA oligomers for dynamic-based SNP (method 1)

| | | |
|---|---|---|
| A | A-antipar | TTT TTT GGA AGA GAT GTA GTA |
| B | G-antipar | TTT TTT GGA ACG GAT GTA GTA |
| C | C-antipar | TTT TTT GGA ACC GAT GTA GTA |
| D | T-antipar | TTT TTT GGA ACT GAT GTA GTA |
| E | A-par | TTT TTT ATG ATG TAG AGA AGG |
| F | C-par | TTT TTT ATG ATG TAG CGA AGG |
| G | G-par | TTT TTT ATG ATG TAG GGA AGG |
| H | T-par | TTT TTT ATG ATG TAG TGA AGG |

Slides were printed using a Genetix Qmini Arrayer and solid pins. A FITC-labelled DNA oligo was used as marker and the following pattern as shown in FIG. 11 was used.

A 2 µM solution of PNA 13 in HybGen buffer (Genetix) was hybridised on the slides using Hyb4 hybridization station (from 65° C. to 40° C. over 6 h and then at 40° C. for 2 hours). After washing the slide was scanned using a Lavision Biotech Scanner a FITC and Cy5 filter sets (FIGS. 12 and 13). FIG. 12 shows the FITC channel and just the marker is detected; in FIG. 13 (Cy5 channel), only the oligos with antiparallel orientation were able to hybridised modified PNA 13

SNP Analysis

Amino modified oligonucleotides (Table 2) were inkjet printed onto aldehyde slides (Genetix) for SNP analysis. These oligos were designed to hybridise following an antiparallel (PNA N-terminal facing DNA 3'-end) orientation when hybridised with PNA 13

TABLE 2

DNA oligomers for dynamic-based SNP

| A | A-antipar Oligo 1 | TTT TTT GGA ACA GAT GTA GTA |
|---|---|---|
| B | G-antipar Oligo 2 | TTT TTT GGA ACG GAT GTA GTA |

Slides were printed using a Microdrop robot and a piezo electric pipette. FIG. 14A shows the pattern used.

A 2 μM solution of PNA 13 in HybGen buffer (Genetix) was hybridised on the slides using Hyb4 hybridization station from 55° C. to 30° C. over 12 h. After washing, the slide was scanned using a Lavision Biotech Scanner. FIG. 14B shows the duplex formed. FIG. 14C (Cy5 channel) show the oligos with antiparallel orientation were able to hybridised modified PNA 13.

Once the arrays were hybridised, aldehyde bases 9 and 10 were incubated with the arrays. Dynamic incorporation was observed when arrays were incubated with 5 μM of each aldehyde together with 1 mM of NaBCNH$_3$ at room temperature for 16 h (see FIG. 14D) at both pH 6 (0.1M NH$_4$OAc) and pH 8.5 (0.2M NaHCO$_3$; 0.3M NaCl). Images obtained using the fluorescein channel (FITC channel) detect DNA oligo 2 (G antiparallel) (FIG. 14D). This signal comes from the base-aldehyde bearing a fluorescein dye, in this case cytosine aldehyde 10, corresponding with the perfect match for G A second approach was also used: To a 2 μM solution of PNA 13 in HybGen buffer (Genetix) aldehydes 9 and 10 at 2 μM concentration were added together with 1 mM NaBCNH$_3$. This solution was used to hybridise a slide containing DNA oligos showed in Table 2. Hybridization occurred from 55° C. to 30° C. over 12 h. Under these conditions, images obtained using the fluorescein channel (FITC channel) detect DNA oligo 2 (G antiparallel: see FIG. 14E). This signal comes from the base-aldehyde bearing a fluorescein dye, in this case cytosine aldehyde 10, corresponding with the perfect match for G.

Solution Based Screening.

Synthesis of PNA Oligomers 12

PNA oligomer 14 (NH$_2$-CATTCTTCCTCT-CONH$_2$) was synthesised using Dde protected monomers (L. Bialy et al., Tetrahedron, 2005, 61, 8295-8305) on solid phase (J. J. Diaz-Mochon et al., Org. Lett. 2004, 6, 1127-1129).

PNA 14 (MALDI-TOF; calculated mass: 3345, found mass: 3348 (M+1) 2 amino modified oligonucleotides complementary to PNA 14 were used for DNA analysis in solution using mass-spec analysis and solid phase analysis.

TABLE 3

DNA oligomers for dynamic-based sequencing and SNP (method 2)

| I | C-extension | TTTTTTAGAGGAAGAATGGGTAA |
|---|---|---|
| J | T-extension | TTTTTTAGAGGAAGAATGAAGTT |

To a 1 μM solution of PNA 14 in HybGen buffer was added a 1.2 μM solution of DNA oligomer I in TE buffer (Table 3). The mixture was heated up to 65° C. and then cool it down slowly to 40° C. At this stage different pH modifications were made before adding PNA monomer aldehyde 2. Extension reaction was followed by HPLC and mass-spectroscopy using reverse phase column and ammonia buffers.

Synthesis of Fluorescently-Labelled PNA Aldehyde Monomers for Dynamic Extension

These compounds were synthesied following modified protocols developed by L. Bialy et al. Tetrahedron, 2006, 61, 8295-8305 for the synthesis of PNA monomers. The main difference is the initial alkylation of ethylendiamine with bromoacetalldehyde diethyl acetal using microwave irradiation (see Scheme 11).

Dde deprotection in solution was achieved using hydrazine and water at room temperature for 16 h. Dye coupling was done using EDCI and HOBt. Final deprotection was achieved using TFA in acetonitrile for 30 min. Purification and analyses were performed as mentioned above.

Scheme 11

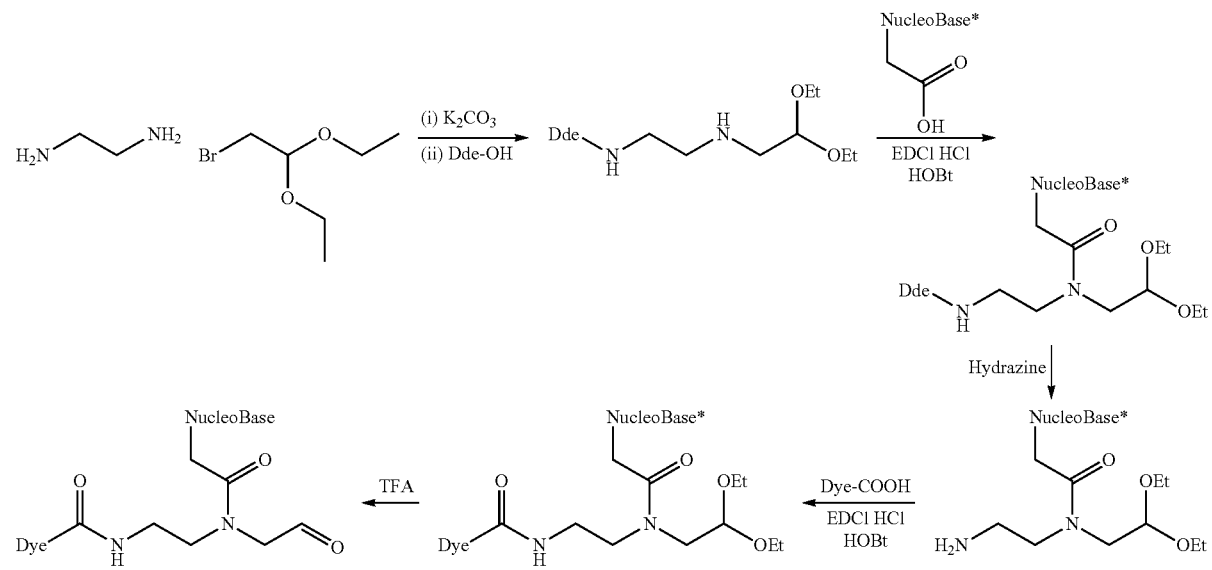

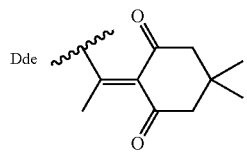
NucleoBase = Adenine*, Guanine*, Cytosine* and Thymine
*protected with acidic-labile protecting group such as methoxytrityl and Boc
As examples, fluorescein-labelled PNA-aldehyde thymine and rhodamine-labelled PNA-aldehyde cytosine were prepared—see scheme 12.
Scheme 12
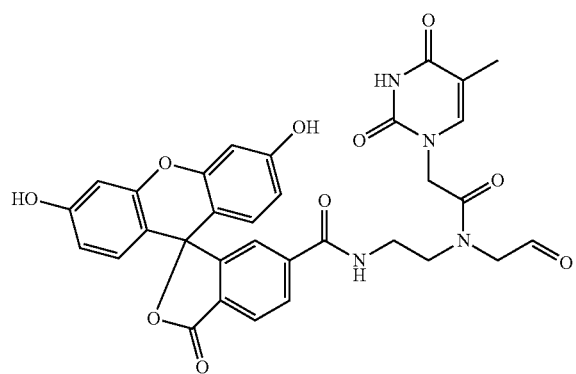
Thymine
15
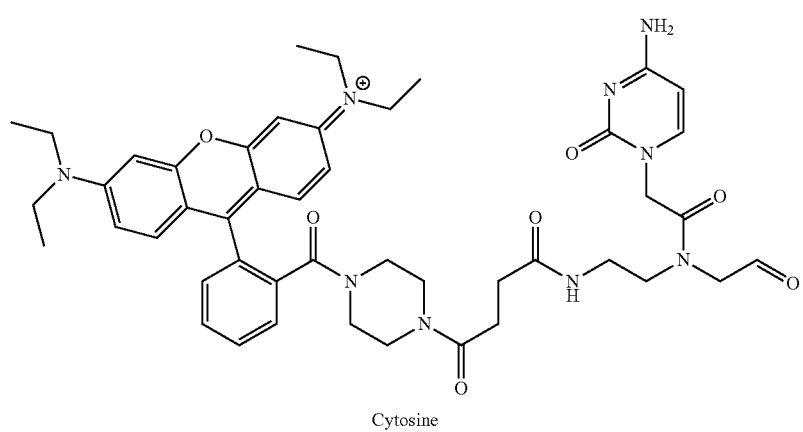
Cytosine
16

One of skill will appreciate that adenine and guanine derivatives using BODIPY dyes will prepare in a similar manner.

Use of Dimers for Sequencing

Figure 15A:
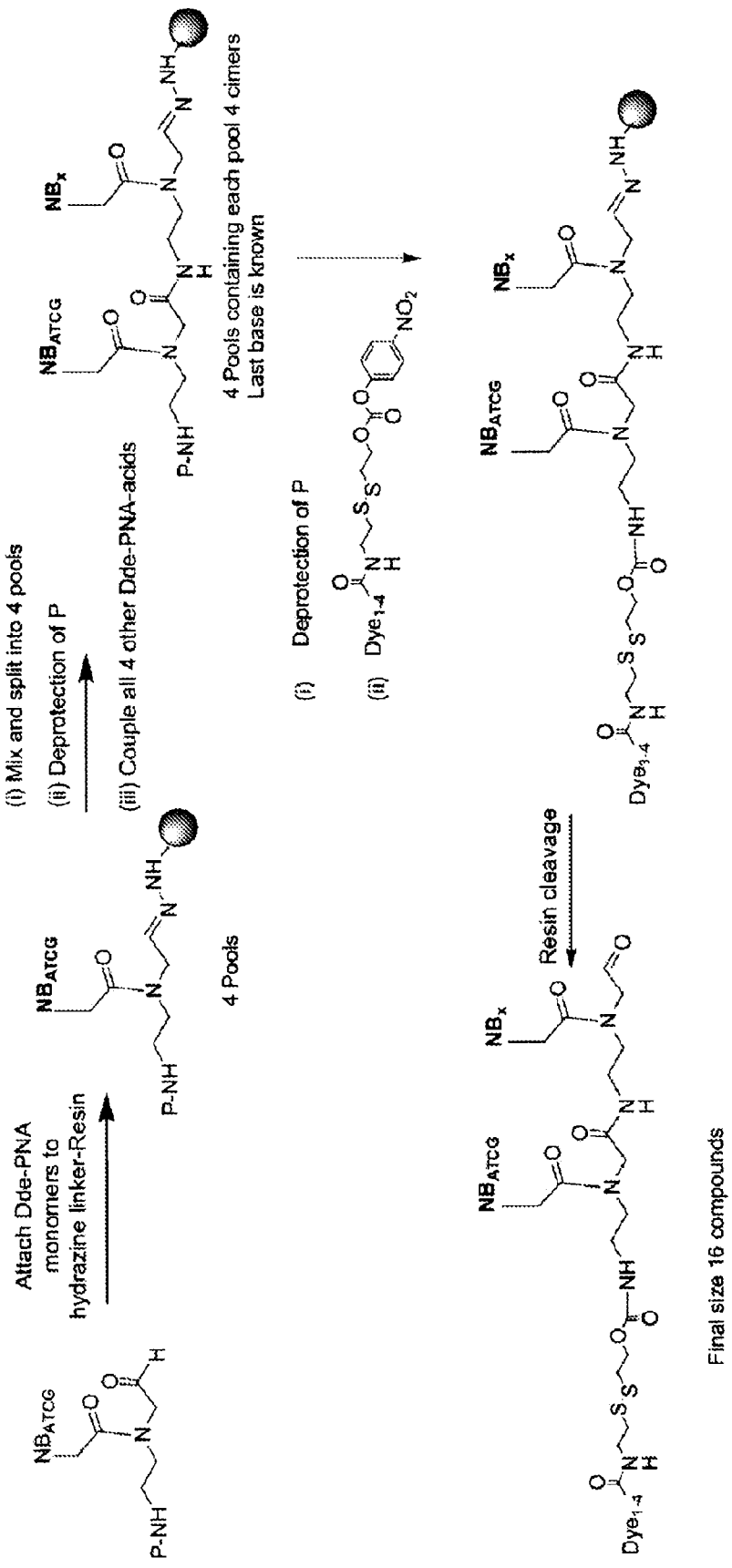

Aldehydes are prepared by attachment to an additional PNA building block. This necessitates the preparation of a mixture of 16 compounds accomplished by solid phase methods using and split and mix strategy. In this case the 4 N-protected aldehydes (A, T, C and G) are immobilised onto either a hydrazine linker (see A. Lee et. al., *J. Am. Chem. Soc.,* 1999, 121, 9907-9914) or threonyl scavenging resin (D. M. Rosenbaum and D. R. Liu, *J. Am. Chem. Soc.,* 2003 125, 13924-13925). The protecting groups are then cleaved and the four resins mixed and split into four pools to couple standard protected PNA monomers. Following deprotection and labelling using activated disulfide (Scheme 13) containing a specific dye according to the last nucleobase, a global mixing of the resin and cleavage gives 16 PNA dimers (FIG. 15A).

FIG. 16 (A and B) details methods of characterising SNPs/nucleotides and/or of sequencing which utilise the PNA dimers/trimers provide by this invention.

Four DNA oligomers attached to the slide varying only in one position (for simplicity only 6 bases are shown). A single complementary PNA sequence is hybridised to the array (again note the PNA will be 12 bases long—only 2 are shown to aid clarity). All 16 PNA-dimer aldehydes are added allowing dynamic attachment of the corresponding dimer. In this case the second base of the dimer will be identified by way of a detectable tag.

Figure 15B:
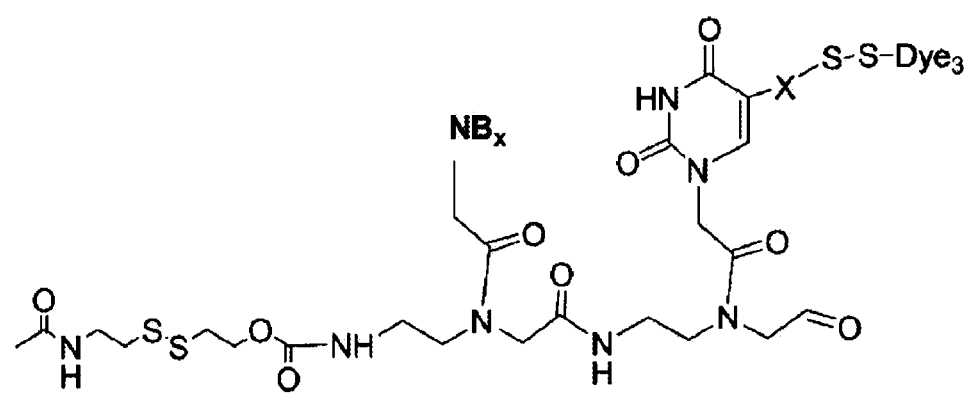

In an alternative embodiment, the dimers are created such that the first nucleobase is identified by means of a detactable tag and the second is random. In this cases the first nucloebase has a dye in the ring while the protecting group does not bear any dye. FIG. 15B shows an example of this form of dimer.

Scheme for Mass Spec Based Detection on Gold-Arrays

Gold surfaces with DNA oligos attached through gold-thiol self-assembly monolayers (SAM) may be used for analysis of genetic material. For example, following the formation of SAM on gold surfaces using thiol-modified DNA oligos and the hybridisation of PNA oligomers, dynamic incroporation using aldehyde-modified nucleobases may be used to characterise SNPs/nucleotides and/or to sequence nuclec acids. As described above, the incorporated base on the PNA strand may be detected by MALDI-TOF (for the use of gold surfaces and detection of PNA-DNA hybridization see Brandt et al/ *Nucleic Acid Research,* 2003, 31, e119).

When conducting SNP analysis, the nucelobases may either be those modified nucleobases substantially described above i.e. having a dye attached to them, unmodified nucleobases or nucleobases modified to include a mass-tag, such as a bromide tag, to give a clear isotopic pattern (FIG. 17).

The general structure of the modified nucleobases for use in mass-based SNP analysis (such as that involving techniques such as MALDI-TOF) are given in FIG. 18.

One of skill will appreciate that a similar "mass-based" analysis approach may be used for sequencing and modified nucleobases which may be useful in such methods are detailed in FIG. 19.

The invention claimed is:

1. A method of characterising a nucleotide in a nucleic acid sequence, said method comprising:
   (a) contacting a nucleic acid with a peptide nucleic acid (PNA) oligomer capable of hybridising to a portion of the nucleic acid and lacking a base complementary to that of the nucleotide to be characterised, to form a nucleic acid/PNA duplex; and
   (b) contacting the nucleic acid/PNA duplex with modified bases selected from the group consisting of:

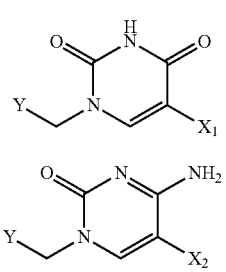

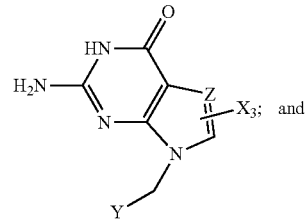

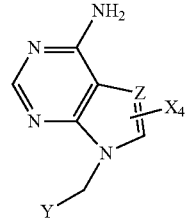

Wherein Y is a functional group capable of reversible covalent reactions;

$X_1$-$X_4$ is a detectable tag, spacer-tag combination or hydrogen; and

Z is carbon or nitrogen;

wherein the modified base which integrates with the nucleic acid/PNA duplex is complementary to that of the nucleotide to be characterised, the nucleotide being characterised by mass spectrometry or by means of the detectable tag of the modified base.

2. The method of claim 1, wherein Y is selected from the group consisting of aldehydes, ketones, thiols and/or diols.

3. The method of claim 1, wherein the peptide nucleic acid oligomer comprises a moiety capable of reacting reversibly with functional group Y of the modified bases.

4. The method of claim 1, wherein the method of characterising a nucleotide is used to characterise single nucleotide polymorphisms.

5. The method of claim 1, wherein the method of characterising a nucleotide is used to sequence nucleic acids.

6. The method of claim 1, wherein the detectable tag is identified by mass spectrometry or microscopy methods.

7. The method of claim 1, wherein the nucleic acid and/or PNA are immobilised on or otherwise bound to, a support substrate.

8. The method of claim 7, wherein the nucleic acid and/or PNA is immobilised or bound as an array or microarray.

9. A modified base selected from the group consisting of:

-continued (iii) 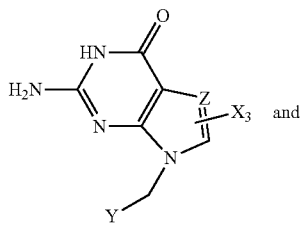 and (iv) 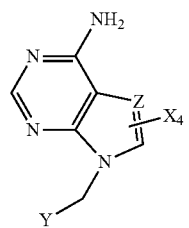

wherein Y is a functional group capable of enzyme free reversible covalent reactions;

$X_1$ is a detectable tag detectable by fluorescent microscopy;

$X_2$-$X_4$ is a detectable tag or spacer tag combination; and

Z is carbon or nitrogen wherein the detectable tag is one or more selected from the group consisting of dansyl, fluorescein, rhodamine, texas red, IAEDANS, cyanine dyes, Bodipy dyes, Alexa Fluor dyes and SNARF dyes.

10. The modified base of claim 9, wherein the detectable tag of $X_2$-$X_4$ is a tag or label which is optically detectable.

11. The modified base of claim 9, wherein the detectable tag of $X_2$-$X_4$ is a mass-tag.

12. The modified base of claim 9, wherein the functional group capable of enzyme free reversible covalent reactions is selected from the group consisting of aldehydes, ketones, thiols and/or diols.

* * * * *

UNITED STATES PATENT AND TRADEMARK OFFICE
CERTIFICATE OF CORRECTION

PATENT NO.        : 8,716,457 B2
APPLICATION NO. : 12/679221
DATED             : May 6, 2014
INVENTOR(S)       : Bradley et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 868 days.

Signed and Sealed this

Twenty-ninth Day of September, 2015

Michelle K. Lee
*Director of the United States Patent and Trademark Office*